(12) United States Patent
Fox et al.

(10) Patent No.: US 10,155,777 B2
(45) Date of Patent: Dec. 18, 2018

(54) TRANS-CYCLOHEPTENES AND HETERO-TRANS-CYCLOHEPTENES FOR BIOORTHOGONAL COUPLING

(71) Applicants: Joseph Fox, Newark, DE (US); Han Zhang, Columbia, MD (US); Yinzhi Fang, Newark, DE (US)

(72) Inventors: Joseph Fox, Newark, DE (US); Han Zhang, Columbia, MD (US); Yinzhi Fang, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 15/564,540

(22) PCT Filed: Apr. 7, 2016

(86) PCT No.: PCT/US2016/026418
§ 371 (c)(1),
(2) Date: Oct. 6, 2017

(87) PCT Pub. No.: WO2016/164565
PCT Pub. Date: Oct. 13, 2016

(65) Prior Publication Data
US 2018/0072761 A1  Mar. 15, 2018

Related U.S. Application Data

(60) Provisional application No. 62/144,360, filed on Apr. 8, 2015.

(51) Int. Cl.
| | | |
|---|---|---|
| C07F 7/08 | (2006.01) |
| C07D 401/14 | (2006.01) |
| C07D 223/04 | (2006.01) |
| C07D 237/26 | (2006.01) |
| C07D 237/30 | (2006.01) |
| C07D 257/08 | (2006.01) |
| C07C 13/24 | (2006.01) |
| C07C 35/20 | (2006.01) |
| C07C 49/547 | (2006.01) |
| G01N 33/58 | (2006.01) |

(52) U.S. Cl.
CPC .......... *C07F 7/0807* (2013.01); *C07C 13/24* (2013.01); *C07C 35/20* (2013.01); *C07C 49/547* (2013.01); *C07D 223/04* (2013.01); *C07D 237/26* (2013.01); *C07D 237/30* (2013.01); *C07D 257/08* (2013.01); *C07D 401/14* (2013.01); *C07F 7/0816* (2013.01); *C07C 2601/18* (2017.05); *G01N 33/58* (2013.01)

(58) Field of Classification Search
None
See application file for complete search history.

(56) References Cited

U.S. PATENT DOCUMENTS

| | | | |
|---|---|---|---|
| 2009/0023916 A1 | 1/2009 | Fox et al. | |
| 2014/0080801 A1* | 3/2014 | Hodges ................ | C07D 401/14 514/210.2 |
| 2014/0093450 A1 | 4/2014 | Robillard et al. | |
| 2015/0005481 A1 | 1/2015 | Chin et al. | |

FOREIGN PATENT DOCUMENTS

| | | |
|---|---|---|
| WO | 2004101558 A1 | 11/2004 |
| WO | WO-2004101558 A1 * | 11/2004 ........... C07D 417/04 |

OTHER PUBLICATIONS

International Search Report and Written Opinion for International Application No. PCT/US2016/026418, dated Jun. 16, 2016, 8 pages.
International Preliminary Report on Patentability for International Application No. PCT/US2016/026418, dated Oct. 10, 2017, 7 pages.
Coates et al., "Electrocyclic Ring Opening of a β-Lithiocyclopropyloxirane. Generation and Trapping of (2Z,4E)-Cyclopheta-2-4-dienol," J. Am. Chem. Soc., vol. 105, 1983, pp. 7322-7326.
Corey et al., Stereospecific Syntheses of Olefins from 1,2-Thionocarbonates and 1,2-Trithiocarbonates. Trans-Cycloheptene. J. Am. Chem. Soc., vol. 87, 1965, pp. 934-935.
Evers et al., "Photocatalysis IV. Preparation and characterization of a stable copper(I) triflate-trans-cycloheptene complex", Journal of the Royal Netherlands Chemical Society, vol. 98, No. 6, 1979, pp. 423-423.
Greene et al., "Diastereoselective synthesis of seven-membered-ring trans-alkenes from dienes and aldehydes by silylene transfer", Journal of the American Chemical Society, vol. 134, No. 30, 2012, pp. 12482-12484.

(Continued)

*Primary Examiner* — Clinton A Brooks
*Assistant Examiner* — Kofi Adzamli
(74) *Attorney, Agent, or Firm* — RatnerPrestia

(57) ABSTRACT

A substituted trans-cycloheptene according to formula (I); wherein: a) Z and L are each selected from the group consisting of $SiR^1R^2$, $CH_2$, CHOH, and $CHR^2$; $R^1$ is phenyl or $CH_3$; $R^2$ is phenyl, $CH_3$, $(CH_2)_nCN$, or $(CH_2)_nOH$, wherein n is an integer from 1 to 5; $R^a$ and $R^b$ are each individually selected from the group consisting of H, OH, and $CH_3$; and Z and L are not both $SiR^1R^2$; or b) Z is BocN, L is $CH_2$, $R^a$ is H, and $R^b$ is H; or c) Z is C=O, L is $CH_2$, $R^a$ is H, and $R^b$ is H.

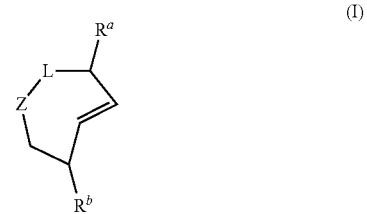

(I)

3 Claims, 2 Drawing Sheets

(56) References Cited

OTHER PUBLICATIONS

Hoffmann et al., "Trapped Optically Active ( E )-Cycloheptene Generated by Enantiodifferentiating Z-E Photoisomerization of Cycloheptene Sensitized by Chiral Aromatic Esters", Journal of the American Chemical Society, vol. 121, No. 46, 1999, pp. 10702-10710.

Hodgson et al., "On the Mechanism of based-induced rearrangements of epoxides to ketones: a formal synthesis of (S)-physoperuvine", Tetrahedron Letters, vol. 40, 1999, pp. 8637-8640.

Huber et al., "Acceleration of the Ortho Ester Claisen Rearrangement by Clay-Catalyzed Microwave Thermolysis: Expeditious Route to Bicycic Lactones", J. Org. Chem., vol. 57, 1992, pp. 5778-5780.

Hurlocker et al., "Structure and Reactivity of an Isolable Seven-Membered-Ring trans -Alkene", Angew. Chem. vol. 127, 2015, pp. 4369-4372.

Inoue et al., "trans-Cycloheptene. Photochemical generation and thermal trans-cis isomerization", Journal of the Chemical Society, Chemical Communications, vol. 20, 1981, pp. 1031-1033.

Jendralla, H., "Cycloadditions with Silver Ion-Stabilized (2RS,3RS)-3-Methoxy-trans-Cycloheptene", Angewandte Chemie International Edition in English, vol. 19, No. 12, 1980, pp. 1032-1033.

Jendralla, H., "(5RS, 6RS)-8-Methoxy-1(Z), 4(E)-cycloheptadien. Erzeugung, Nachweis und Folgereaktionen", Chem. Ber., vol. 113, 1980, pp. 3557-3569.

Krebs et al., "Synthesis of enantiomerically pure (E)-1,1,3,3,6,6-hexamethyl-1-sila-4-cycloheptene and its absolute configuration", Tetrahedron: Asymmetry, vol. 10, No. 18, 1999, pp. 3483-3492.

Krebs et al., "A Stable Hetero-trans-cyclopentene", Angewandte Chemie International Edition in English, vol. 36, No. 1/2, 1997, pp. 159-160.

Li et al., "Diels-Alder reaction-triggered bioorthogonal protein decaging in living cells", Nature Chemical Biology, vol. 10, 2014, pp. 1003-1007.

Marshall, J. A., "Photosensitized ionic additions to cyclohexenes", Accounts of Chemical Research, vol. 2, No. 2, 1969, pp. 33-40.

Matsuo et al., "Intramolecular formal [4+2] cycloaddition of 3-ethoxycyclobutanones and alkenes", Chem. Commun., vol. 46, 2010, pp. 934-936.

Nishiyama et al. Chiral Bis(dihydrooxazolyl)pyridinenuthenium Complexes of trans-Cyclooctene and trans-Cycloheptene. Chemistry—A European Journal, vol. 5, No. 12, 1999, pp. 3509-3513.

Salomon et al., "Copper(I) catalysis in photocycloadditions. II. Cyclopentene, cyclohexene, and cycloheptene", Journal of the American Chemical Society, vol. 96, No. 4, 1974, pp. 1145-1152.

Squillacote et al., "How Stable Is trans-Cycloheptene?", Journal of the American Chemical Society, vol. 127, No. 45, 2005, pp. 15983-15988.

Tomooka et al , "Planar chiral dialkoxysilane: Introduction of inherent chirality and high reactivity in conventional achiral alkene", Chemistry—A European Journal, vol. 20, No. 25, 2014, pp. 7598-7602.

Versteegen et al., "Click to Release: Instantaneous Doxorubicin Elimination upon Tetrazine Ligation", Angewandte Chemie International Edition in English, vol. 52, 2013, pp. 14112-14116.

Wallraff et al., "Low-temperature reactions of copper(I) triflate complexes of cis- and trans-cyclooctene and cis- and trans-cycloheptene with trimethyl phosphite. Spectroscopic evidence for free trans-cycloheptene", The Journal of Organic Chemistry, vol. 51, 10, 1986, pp. 1794-1800.

Wilson et al., "Synthesis of Homoallylic Alcohols in Aqueous Media", J. Org. Chem., vol. 54, 1989, pp. 3087-3091.

Spee et al., "Photocatalysis. 6. On the mechanism of the cyclotrimerization of trans-cycloheptene, catalyzed by copper (I) triflate", Journal of the American Chemical Society, vol. 103, No. 23, 1981, pp. 6901-6904.

Kuhn et al., "Low Catalyst Loadings in Olefin Metathesis: Synthesis of Nitrogen Heterocycles by Ring-Closing Metathesis", Organic Letters, vol. 12, No. 5, 2010, pp. 984-987.

\* cited by examiner

TRANS-CYCLOHEPTENES AND HETERO-TRANS-CYCLOHEPTENES FOR BIOORTHOGONAL COUPLING

CROSS REFERENCE TO RELATED APPLICATIONS

This application a U.S. National Phase filing of International Application PCT/US2016/026418, filed 7 Apr. 2016, and claims priority benefit of U.S. Pat. Appln. No. 62/144,360, filed 8 Apr. 2015, the entirety of which applications are incorporated herein by reference for all purposes.

STATEMENT REGARDING FEDERALLY SPONSORED RESEARCH

This invention was made with government support under Contract No. R01 EB014354 01 A1, awarded by the National Institutes of Health, and under contract number DMR1206310, awarded by the National Science Foundation. The government has certain rights in the invention.

FIELD OF THE INVENTION

The invention relates to trans-cycloheptenes, hetero-trans-cycloheptenes, and their uses.

BACKGROUND OF THE INVENTION

For many years, the unusual bonding, reactivity and planar chirality of trans-cycloalkenes have captured the imagination of scientists. trans-Cyclooctene—the most broadly studied trans-cycloalkene—is resolvable and has a high barrier to racemization ($E_a$=35.6 kcal/mol). The double bond of trans-cyclooctene is twisted severely in the crown conformation, and as a consequence the HOMO of trans-cyclooctene is high in energy relative to cis-cyclooctene, leading to unusual reactivity. The high reactivity of trans-cyclooctenes has recently produced an impressive resume of applications in synthesis, including reactions with dienes, 1,3-dipoles and ketenes, and strained trans-cyclooctenes can serve as excellent ligands for transition metals. In addition to their usefulness in synthesis, trans-cyclooctenes hold special significance in the field of bioorthogonal chemistry due to their particularly fast kinetics in Diels-Alder reactions with tetrazines. But despite these advances, there remains a need for additional options for conducting bioorthogonal coupling reactions with tetrazines and other compounds.

SUMMARY OF THE INVENTION

The invention provides a substituted trans-cycloheptene according to formula (I)

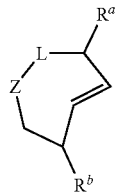

(I)

wherein:
a) Z and L are each selected from the group consisting of $SiR^1R^2$, $CH_2$, CHOH, and $CHR^2$; $R^1$ is phenyl or $CH_3$; $R^2$ is phenyl, $CH_3$, $(CH_2)_nCN$, or $(CH_2)_nOH$, wherein n is an integer from 1 to 5; $R^a$ and $R^b$ are each individually selected from the group consisting of H, OH, and $CH_3$; and Z and L are not both $SiR^1R^2$; or b) Z is BocN, L is $CH_2$, $R^a$ is H, and $R^b$ is H; or
c) Z is C=O, L is $CH_2$, $R^a$ is H, and $R^b$ is H.

The invention also provides a method of performing a bioorthogonal coupling reaction, comprising contacting a tetrazine, ketene, conjugated diene, or 1,3-dipole, in each case substituted with a biomolecule, with a trans-cycloheptene or a hetero-trans-cycloheptene.

DETAILED DESCRIPTION OF THE INVENTION

Figure 1:
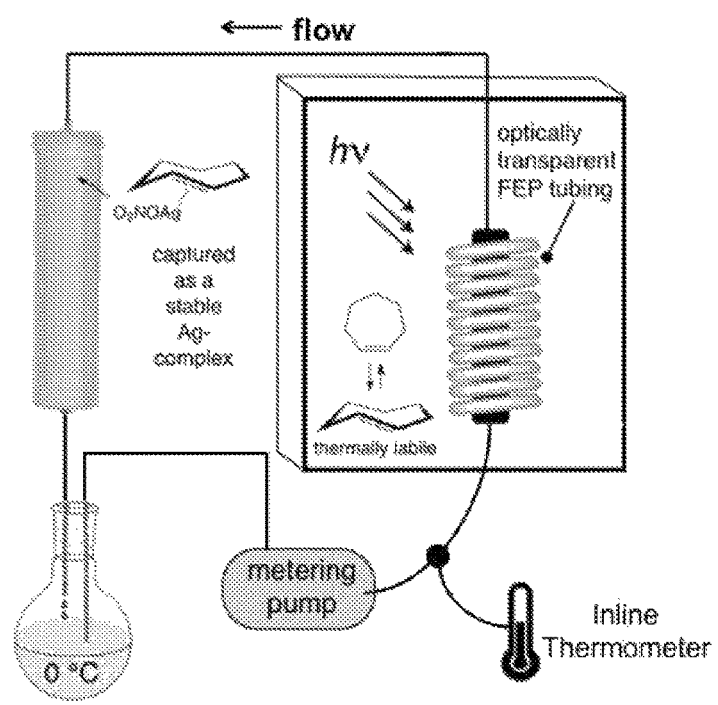
FIG. 1 is a schematic diagram of an apparatus for preparing trans-cycloheptenes and hetero-trans-cycloheptenes according to the invention.
Figure 2:
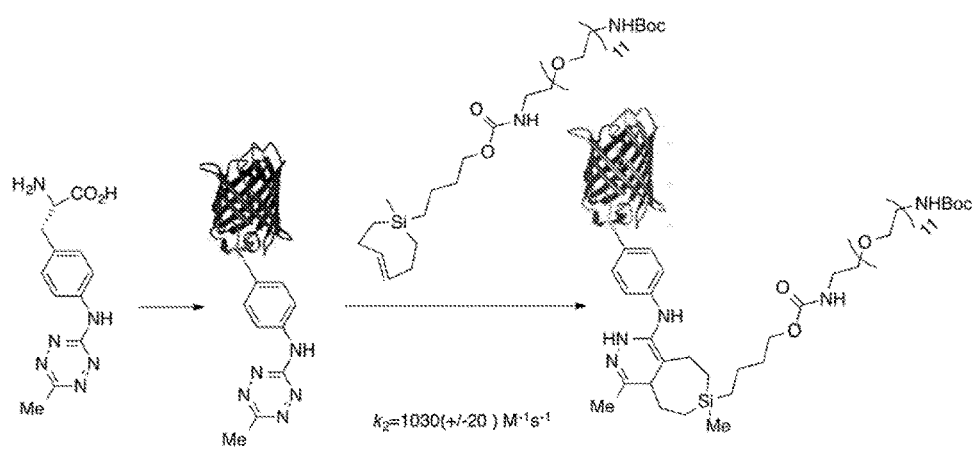
FIG. 2 shows Scheme 4 depicting in vitro Green Fluorescent Protein (GFP) labeling experiment to illustrate ligation reaction between a tetrazine-modified Protein and a sila-trans-cycloheptene, in accordance with various embodiment of the present invention.

The inventors have now prepared novel trans-cycloheptenes and hetero-trans-cycloheptenes, and found that they show remarkable potential for utility in bioorthogonal coupling reactions. These compounds can be prepared by photoisomerization and captured as Ag-complexes, using a flow method for photoisomerization of trans-cyclooctene in which the cis/trans equilibrium is driven by selective complexation of the trans-cyclooctene on $AgNO_3$-impregnated silica gel. Due to the thermal lability of trans-cycloheptenes, the inventors used the reactor design depicted in FIG. 1. In this configuration a reservoir of chilled solvent is positioned before the photowell, and the photoisomerization is conducted in a coil of optically transparent FEP [Fluorinated Ethylene Propylene] tubing. The fluoropolymer tubing provides a high surface area and minimal volume (only 30 mL for 8 m tubing), thereby minimizing the time delay between photoisomerization and product adsorption on $AgNO_3$/silica. The trans-cycloheptene.$AgNO_3$ complexes are eluted from the column and isolated as solids that are stable for weeks in a freezer.

Examples illustrating the scope of photochemical trans-cycloheptene and sila-trans-cycloheptene syntheses using the described apparatus are shown in Tables 1 and 2, respectively. The method was successful for the synthesis of trans-cycloheptenes bearing nitrile, hydroxyl, phenyl, and alkyl substituents. A variety of annulated products and a dihydroxylation product were prepared from the trans-cycloheptenes and sila-trans-cycloheptenes (Table 3). trans-Cycloheptenes and hetero-trans-cycloheptenes, for example sila-trans-cycloheptenes, rapidly form Diels-Alder adducts with tetrazines, and also with ketenes, conjugated dienes, organic azides, diazo compounds, and other 1,3-dipoles, any of which may be unsubstituted or substituted with one or more substituents attached either directly or via a linking or spacer group. Exemplary substituents comprise biological molecules. Suitable biological molecules may be endogenous or exogenous, and may for example include large macromolecules such as proteins, carbohydrates, lipids, and nucleic acids, as well as small molecules such as primary metabolites, secondary metabolites, and natural products. For example, the substituent(s) may comprise peptides, oligopeptides, or polypeptides. Fleming-Tamao reaction with (5aS,6R,9S,9aS)-3,3-diphenyl-2,3,4,5,5a,6,9,9a-octahydro-1H-6,9-methanobenzo[d]silepine (entry 4 in Table 3) provided the corresponding ring-opening product 2,2'-((1R,2S,3S,4S)-bicyclo[2.2.1]hept-5-ene-2,3-diyl)bis(ethan-1-ol) (Scheme 1).

Scheme 1. Fleming-Tamao Oxidation
TABLE 1
Synthesis of trans-cycloheptene derivatives
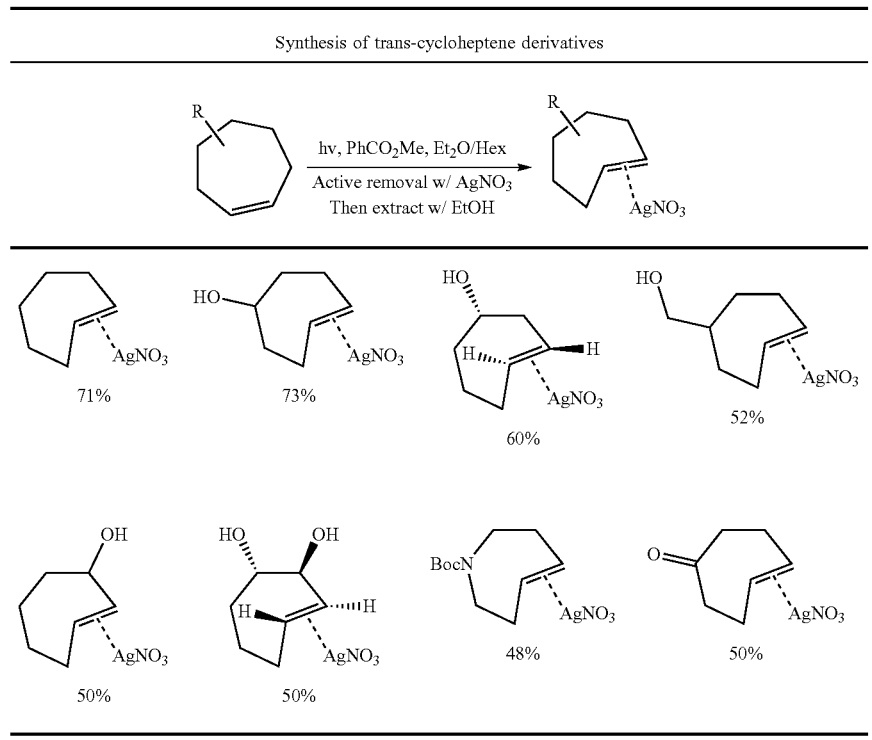
TABLE 2
Synthesis of sila trans-Cycloheptene derivatives
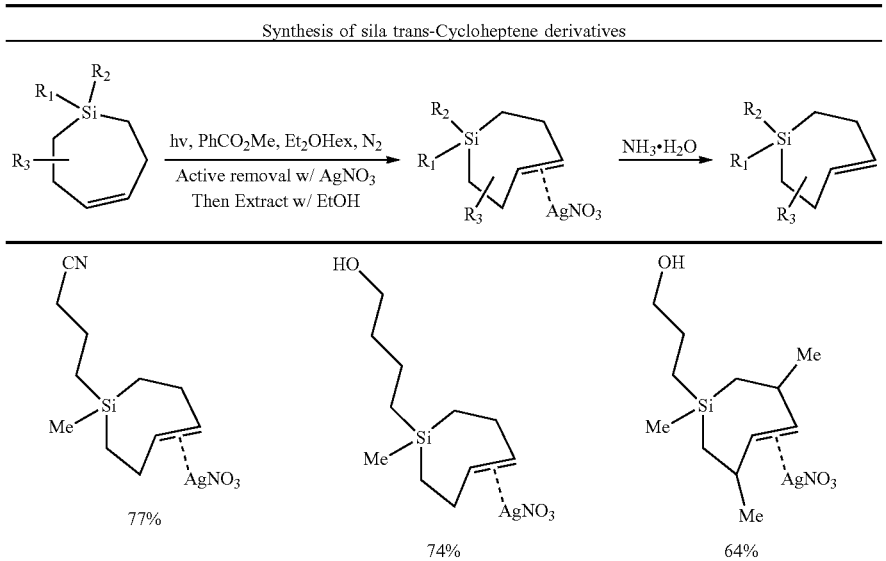

TABLE 2-continued
Synthesis of sila trans-Cycloheptene derivatives
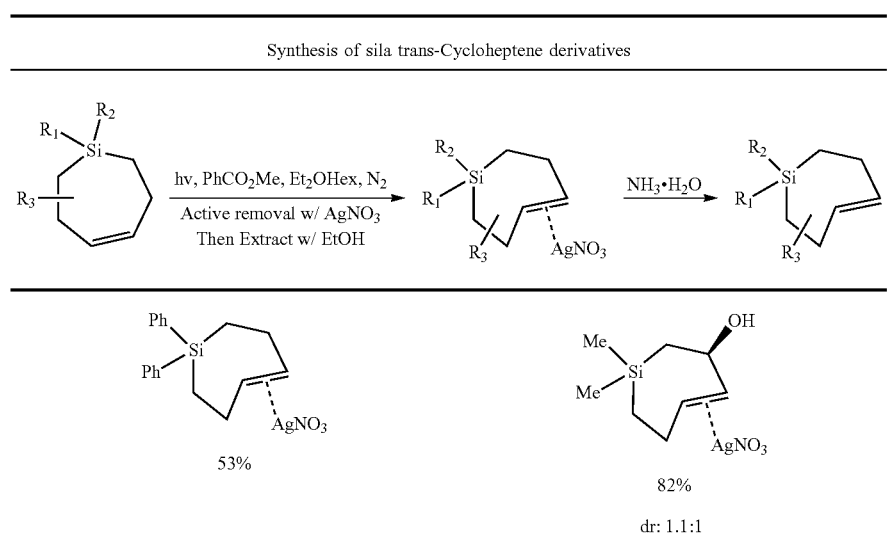
53%
82%
dr: 1.1:1
TABLE 3
Reactivity experiments
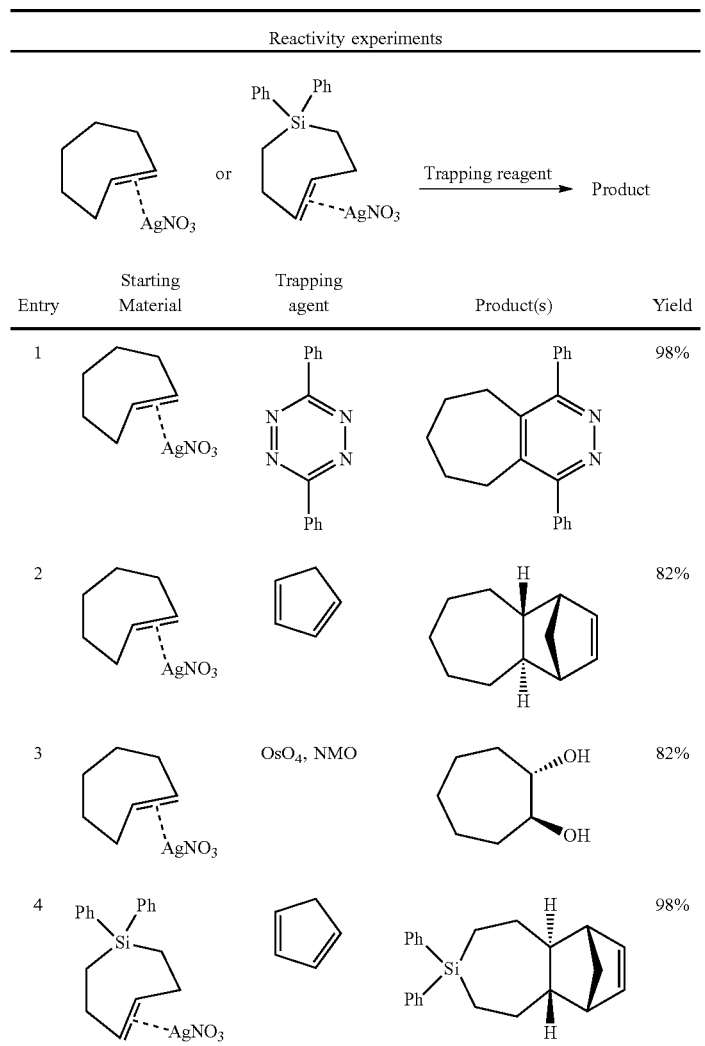

TABLE 3-continued

Reactivity experiments

| Entry | Starting Material | Trapping agent | Product(s) | Yield |
|---|---|---|---|---|
| 5 | Ph₂Si-silacycloheptene·AgNO₃ | $CH_2N_2$ | bicyclic pyrazoline product | 65% |
| 6 | Ph₂Si-silacycloheptene·AgNO₃ | Cl₂C=C=O | dichlorocyclobutanone fused product | 78% |
| 7 | Ph₂Si-silacycloheptene·AgNO₃ | Ph-CH₂-N₃ | bicyclic triazoline product | 90% |

EXAMPLES

The following examples illustrate preparation and reactions of trans-cycloheptenes and hetero-trans-cycloheptenes according to the invention.

Stability of Ag-Free (E)-Si-(4-hydroxybutyl)-Si-methyl-5-silacycloheptene

Both trans-cycloheptene.AgNO₃ and sila-trans-cycloheptene.AgNO₃, as well as essentially any substituted analog of these, can be desalted by treatment with aqueous NaCl to remove the AgNO₃ complexing agent. A typical "desalting" procedure was performed on (E)-Si-(4-hydroxybutyl)-Si-methyl-5-silacycloheptene.AgNO₃. In an NMR experiment, (E)-Si-(4-hydroxybutyl)-Si-methyl-5-silacycloheptene.AgNO₃ (0.3 mmol) was treated with 5 mL brine solution and 3 mL $C_6D_6$. The $C_6D_6$ layer was separated and dried over $Na_2SO_4$. The $C_6D_6$ solution was directly used in the NMR experiment, in which Ag-free (E)-Si-(4-hydroxybutyl)-Si-methyl-5-silacycloheptene (with 2% cis-isomer) was recovered and observed by $^1H$ NMR.

The stability of Ag-free (E)-Si-(4-hydroxybutyl)-Si-methyl-5-silacycloheptene was studied. (E)-Si-(4-hydroxybutyl)-Si-methyl-5-silacycloheptene (98:2 trans:cis) was stored as a diethyl ether solution (4.3 mg/mL) in freezer (−15° C.). Over a period of 36 days, the ratio of trans isomer to cis isomer changed by only one percent (97:3 trans:cis), indicating the stability of (E)-Si-(4-hydroxybutyl)-Si-methyl-5-silacycloheptene in solution at low temperature.

Bioorthogonal Coupling Reaction with Tetrazines

The rate of the reaction between (E)-Si-(4-hydroxybutyl)-Si-methyl-5-silacycloheptene and tetramethylrhodamine-conjugated dipyridyl tetrazine was studied. The results are shown in Scheme 2. With a rate constant that exceeds $10^7$ $M^{-1}s^{-1}$ (Scheme 2), (E)-Si-(4-hydroxybutyl)-Si-methyl-5-silacycloheptene is the most reactive dienophile to date for bioorthogonal applications. As the reaction was too rapid for reliable rate determination by UV-vis kinetics, the inventors determined the rate of the reaction by the restoring of fluorescence after tetrazine ligation at low concentration in 9:1 $H_2O$:MeOH at 25° C. by using an SX 18MV-R stopped-flow spectrophotometer (Applied Photophysics Ltd.). This is depicted in Scheme 4.

A conjugatable derivative of sila-trans-cycloheptene.AgNO₃ was prepared by treatment with p-nitrophenylchloroformate to give the activated carbonate.AgNO₃ in 22% yield, and this was readily conjugated to several amines under standard conditions, as depicted in Scheme 3.

Scheme 2. Comparison of second order rate constants

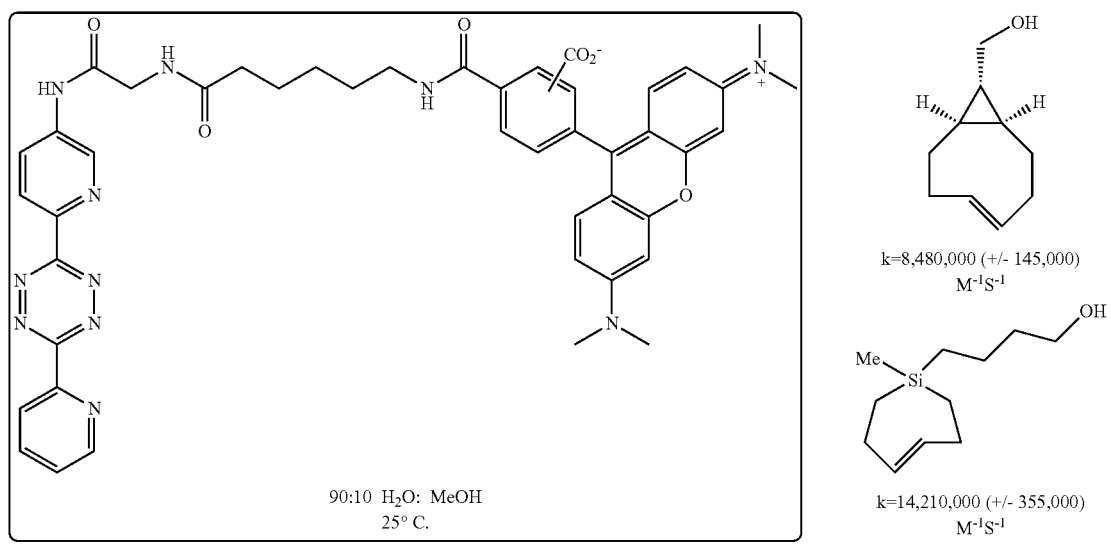

Scheme 3. Synthesis of sila trans-cycloheptene derivatives.

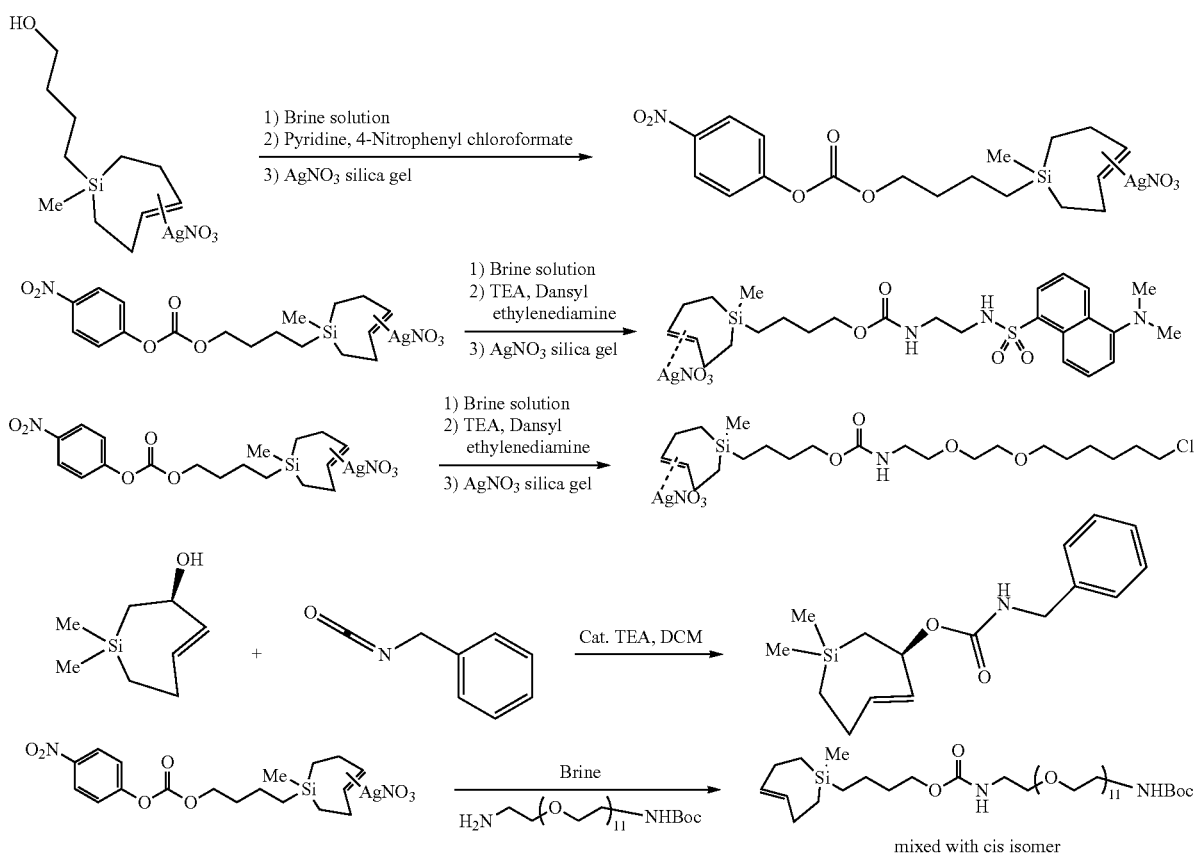

In Vitro Kinetic Analysis of Sila-Trans-Cycloheptene Ligation with a Tetrazine-Modified Protein Tetrazines quench the fluorescence of Green Fluorescent Protein (GFP) when attached to it, providing a probe to measure the kinetics of the ligation reaction between the tetrazine and a sila-trans-cycloheptene. After tetrazine ligation the fluorescence is restored, thus providing a convenient handle for monitoring the reaction. With sila-trans-cycloheptene, in vitro labeling takes place rapidly with rate constant of $k_2=1030$ (+/−20) $M^{-1}s^{-1}$ to give conjugates (Scheme 4).

Release of Leaving Groups from Tetrazine/Sila-Trans-Cycloheptene Adducts

The cycloaddition reaction between sila-trans-cycloheptene and tetrazine results in an intermediate that rearranges by expulsion of dinitrogen in a retro-Diels-Alder cycloaddition to a 4,5-dihydropyridazine, which may tautomerize to a 1,4-dihydropyridazine, especially under aqueous conditions. Depending on the substituents, the dihydropyridazine can be converted into an aromatic pyridazine in the presence of an oxidant, such as dioxygen. More importantly, a leaving group can be eliminated from the vinyl position or through a double-bond shift (Scheme 5). This illustrates the principle that molecular release can be triggered by tetrazine ligation with a Si-trans-cycloheptene. Previously, Robillard and coworkers had shown that trans-cyclooctene derivatives with allylic leaving groups could be employed to release doxorubicin upon tetrazine ligation. Versteegen, R. M.; Rossin, R.; ten Hoeve, W.; Janssen, H. M.; Robillard, M. S. Click to release: instantaneous doxorubicin elimination upon tetrazine ligation. *Angew. Chem. Int. Ed. Engl.* 2013, 52, 14112. Chen and coworkers demonstrated that a similar decaging strategy could be used for payload delivery in living cells. Li, J.; Jia, S.; Chen, P. R. Diels-Alder reaction-triggered bioorthogonal protein decaging in living cells. *Nat. Chem. Biol.* 2014, 10, 1003. However, both of these approaches rely on trans-cyclooctenes with allylic substitution, substrates that undergo tetrazine ligation with relatively slow kinetics. The faster kinetics of Si-trans-cycloheptenes is anticipated to be a better system for the targeted release of various payloads including drugs and gene activating molecules.

Preparation of Cis-Cycloheptene and Hetero-Cis-Cycloheptene Derivatives (4Z)-tert-Butyl-2,3,6,7-tetrahydro-1H-azepine-1-carboxylate

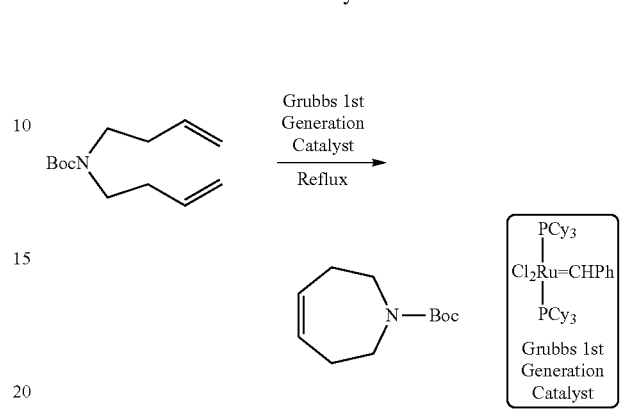

A 1 L round-bottomed flask equipped with a reflux condenser was charged with 500 mL of dichloromethane (DCM), followed by addition of tert-butyl di(but-3-en-1-yl) carbamate (1.00 g, 4.44 mmol), prepared according to the method of Kuhn, K. M. et al., *Organic Letters* 2010 12 (5), 984-987. The solution was heated up to 45° C. Grubbs 1$^{st}$ generation catalyst (238 mg, 0.289 mmol) was added. The reaction mixture was allowed to reflux at 45° C. for 2 hours. The solvent was removed with a rotary evaporator. Purification by column chromatography with 4% ethyl acetate in hexanes yielded 790 mg (4.01 mmol, 90%) of the title compound as an oil.

Scheme 5. Benzylamine release mechanism

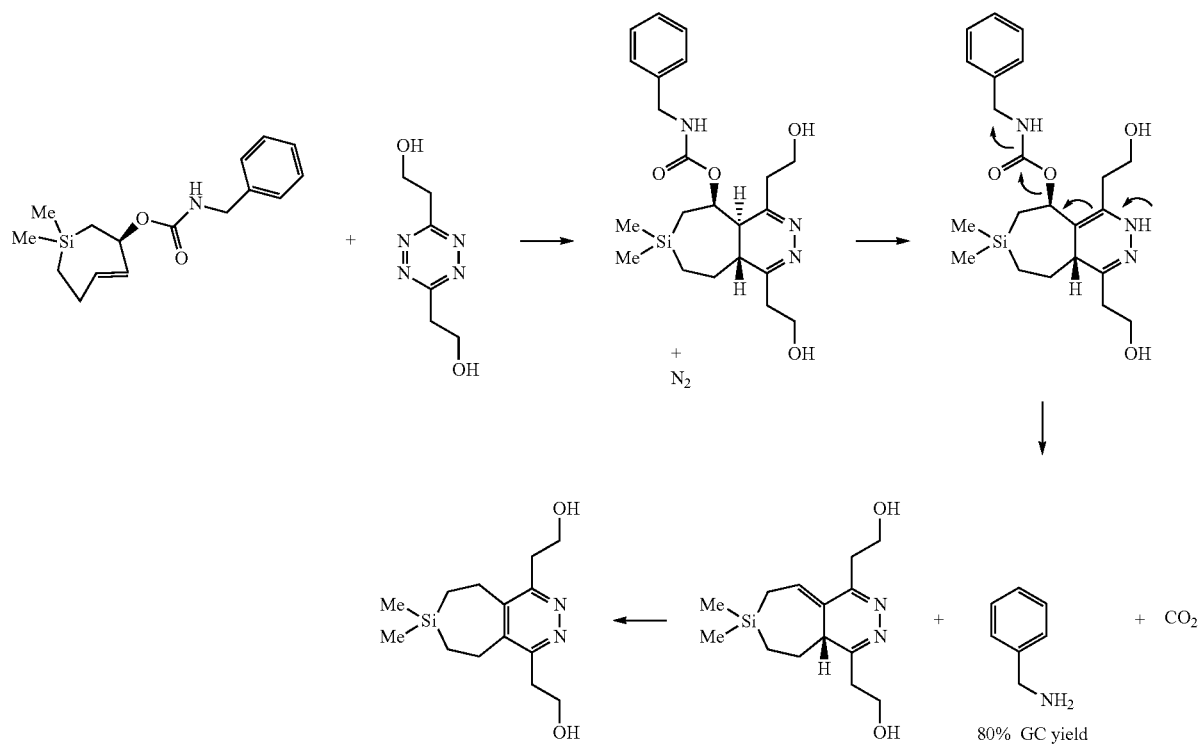

(4Z)-Cyclohept-4-en-1-ylmethanol

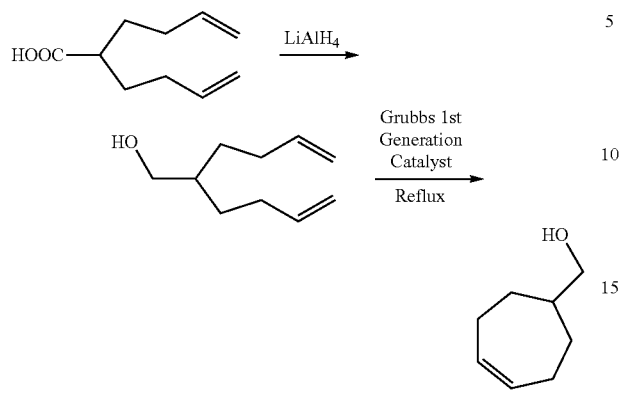

A dry two-neck round-bottomed flask equipped with a reflux condenser was sequentially charged with anhydrous THF (15 mL) and LiAlH$_4$ (780 mg, 20.5 mmol). The mixture was chilled by an ice bath, and a solution of 2-(but-3-en-1-yl)hex-5-enoic acid (2.30 mg, 13.7 mmol, prepared according to the method of Matsuo, J. et al., Chem. Commun. 2010, 46, 934-936) in anhydrous THF (15 mL) was added dropwise syringe. The reaction mixture was then heated to reflux for 24 hours. The reaction mixture was then allowed to cool to room temperature and then to ice bath temperature, and 20 mL of 15% NaOH solution was added dropwise. The resulting mixture was filtered and the filter cake was washed with ethyl ether (30 mL). The aqueous phase was extracted with ethyl ether (3×20 mL) and the combined organics were washed with brine (3×20 mL). The resulting solution was dried with MgSO$_4$, filtered and concentrated on the rotary evaporator. Purification by column chromatography with a gradient of 4% ethyl acetate in hexanes yielded 2-(but-3-en-1-yl)hex-5-en-1-ol (2.00 g, 13.0 mmol, 95%) as a clear oil.

A 2 L round-bottomed flask equipped with a reflux condenser was charged with 1 L of dichloromethane, followed by addition of 2-(but-3-en-1-yl)hex-5-en-1-ol (1.00 g, 6.49 mmol). The solution was heated up to 45° C. Grubbs 1$^{st}$ generation catalyst (267 mg, 0.324 mmol) was added. The reaction mixture was allowed to reflux at 45° C. for 3 hours. The solvent was removed with a rotary evaporator. Purification by column chromatography with 8% ethyl acetate in hexanes yielded 430 mg (3.41 mmol, 54%) of the title compound as a green oil.

(3Z)-Cyclohept-3-en-1-ol

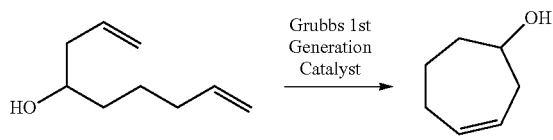

A 1 L round-bottomed flask equipped with a reflux condenser was charged with 350 mL of dichloromethane, followed by addition of nona-1,8-dien-4-ol (355 mg, 2.54 mmol), prepared according to the method of Wilson, S. R. et al., J. Org. Chem. 1989, 54, 3087. The solution was heated up to 45° C. Grubbs 1$^{st}$ generation catalyst (120 mg, 0.146 mmol) was added. The reaction mixture was allowed to reflux at 45° C. for 4 hours. The solvent was removed with a rotary evaporator. Purification by column chromatography with 10% ethyl acetate in hexanes yielded 196 mg (1.75 mmol, 69%) of the title compound as an oil.

(4Z)-Cyclohept-4-en-1-one

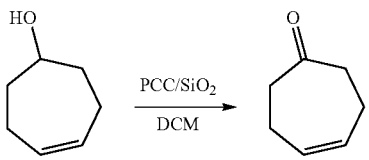 [SMILES: OC1CCC=CCC1 ; O=C1CCC=CCC1]

To a solution of (4E)-cyclohept-4-en-1-ol (525 mg, 4.69 mmol, prepared according to the method of Hodgson, D. M. et al., Tetrahedron Lett. 1999, 40, 8637) was added silica gel (1.30 g) followed by the addition of pyridinium chlorochromate (PCC, 1.11 g, 5.14 mmol). The mixture was allowed to stir at room temperature for 18 hours, and an extra portion of silica gel (1.30 g) was added followed by filtration. The filter cake was washed by ethyl ether, and the filtrate was concentrated on the rotary evaporator. Purification by column chromatography with 10% ethyl ether in pentane afforded title compound (275 mg, 2.50 mmol, 53%) as a clear oil.

4-(Di(but-3-en-1-yl)(methyl)silyl)butanenitrile

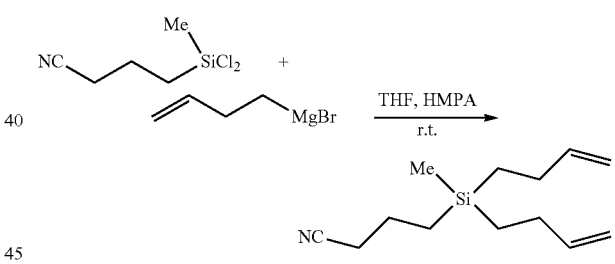

A dry round-bottomed flask was charged with Mg (1.24 g, 51.7 mmol, 3.00 equiv) and dry THF (125 mL) under nitrogen atmosphere. 4-Bromo-1-butene (5.60 mL, 55.2 mmol, 3.21 equiv) was introduced to the flask dropwise via syringe. The reaction mixture was allowed to stir at room temperature. After the formation of the Grignard reagent was judged complete, HMPA (15.0 mL, 86.0 mmol, 5.00 equiv) was added, followed by 4-(dichloro(methyl)silyl)butanenitrile (2.70 mL, 17.2 mmol, 1.00 equiv). The reaction mixture was stirred at room temperature overnight. After reaction, THF was removed via rotary evaporation. Saturated aq. NH$_4$Cl (80 mL) and ethyl acetate (80 mL) were added and the aqueous layer was extracted three times with ethyl acetate. The organics were combined, dried with anhydrous MgSO$_4$, filtered, and concentrated via rotary evaporation. Purification by flash column chromatography (1% diethyl ether/hexane) afforded the title compound as a colorless oil (2.14 g, 9.66 mmol, 56% yield). $^1$H NMR (600 MHz, CDCl$_3$) δ: 5.86 (ddt, J=16.5, 10.1, 6.3 Hz, 2H), 5.00 (dd, J=17.0, 1.7 Hz, 2H), 4.91 (dd, J=10.1, 1.3 Hz, 2H), 2.36 (t, J=6.9 Hz, 2H), 2.05 (ddd, J=9.9, 8.8, 6.4 Hz, 4H), 1.68-1.63

(m, 2H), 0.71-0.68 (m, 2H), 0.67-0.64 (m, 2H), 0.01 (s, 3H); $^{13}$C NMR (150 MHz, CDCl$_3$) δ: 141.3 (CH), 119.8 (C), 113.2 (CH$_2$), 27.9 (CH$_2$), 21.1 (CH$_2$), 20.7 (CH$_2$), 13.8 (CH$_2$), 12.8 (CH$_2$), −5.2 (CH$_3$).

(Z)—Si-(3-Cyanopropyl)-Si-methyl-5-sila-cycloheptene

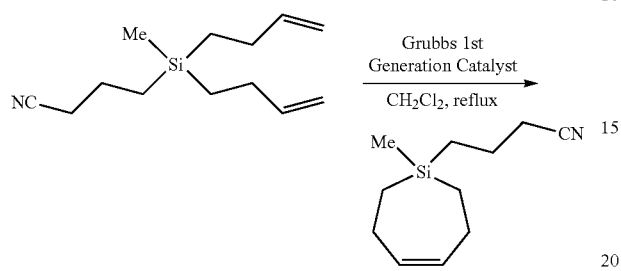

4-(Di(but-3-en-1-yl)(methyl)silyl)butanenitrile (400 mg, 1.81 mmol, 1.00 equiv) was dissolved in dry dichloromethane (120 mL). Grubbs' 1$^{st}$ generation catalyst (74.3 mg, 0.0903 mmol, 0.0500 equiv) was added as a solution in dry dichloromethane (37 mL) and the solution was heated to reflux for 5 hours. After cooling to room temperature, the reaction mixture was concentrated via rotary evaporation. Purification by flash column chromatography (1% diethyl ether/hexane) afforded the title compound (299 mg, 1.55 mmol, 85% yield) as a colorless oil. $^1$H NMR (600 MHz, CDCl$_3$) δ: 5.80-5.72 (m, 2H), 2.35 (t, J=7.0 Hz, 2H), 2.24-2.19 (m, 4H), 1.70-1.62 (m, 2H), 0.72-0.67 (m, 2H), 0.65-0.61 (m, 4H), 0.03 (s, 3H); $^{13}$C NMR (100 MHz, CDCl$_3$) δ: 132.6 (CH), 119.9 (C), 21.1 (CH$_2$), 21.0 (CH$_2$), 14.7 (CH$_2$), 12.5 (CH$_2$), −4.0 (CH$_3$).

(Z)—Si-(4-Oxobutyl)-Si-methyl-5-silacycloheptene

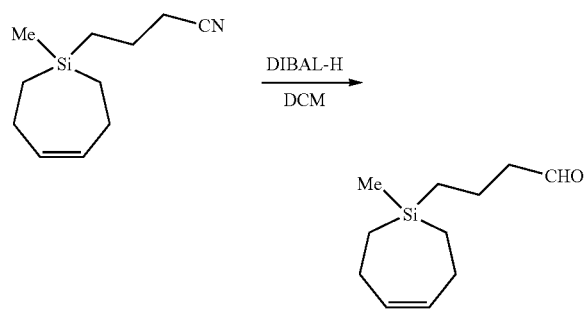

A round-bottomed flask was charged with a solution of (Z)—Si-(3-Cyanopropyl)-Si-methyl-5-silacycloheptene (656 mg, 3.39 mmol, 1.00 equiv) in dichloromethane (4.5 mL) under an atmosphere of nitrogen. The flask was cooled by a bath of dry ice/acetone (−78° C.), and DIBAL-H (4.1 mL of a 1.0 M solution in dichloromethane, 4.1 mmol, 1.2 equiv) was slowly added via syringe. The dry ice/acetone bath was then replaced with a −40° C. bath (dry ice/acetonitrile), and stirring was continued for 1 hour. The cold bath was then replaced by an ice bath (0° C.). At 0° C., H$_2$O (0.14 mL) and 15% NaOH (0.14 mL) were sequentially added dropwise. Additional water (0.34 mL) was added, and the ice bath was removed and the mixture allowed to stir for 15 min at r.t. Some anhydrous magnesium sulfate was added and stirred for another 15 min. The mixture was filtered to remove solids, which were rinsed with excess dichloromethane. The dichloromethane solution were combined and concentrated. Purification by flash column chromatography (15% diethyl ether/hexane, R$_f$=0.48) afforded the title compound (422 mg, 2.15 mmol, 63% yield) as a colorless oil. $^1$H NMR (400 MHz, CDCl$_3$) δ: 9.75 (t, J=1.8 Hz, 1H), 5.80-5.72 (m, 2H), 2.45 (td, J=7.2, 1.8 Hz, 2H), 2.23-2.18 (m, 2H), 1.68-1.60 (m, 2H), 0.64-0.54 (m, 6H), 0.02 (s, 3H); $^{13}$C NMR (100 MHz, CDCl$_3$) δ: 203.2 (CH), 132.7 (CH), 47.7 (CH$_2$), 21.1 (CH$_2$), 16.7 (CH$_2$), 14.8 (CH$_2$), 12.6 (CH$_2$), −4.0 (CH$_3$).

(Z)—Si-(4-hydroxybutyl)-Si-methyl-5-silacycloheptene

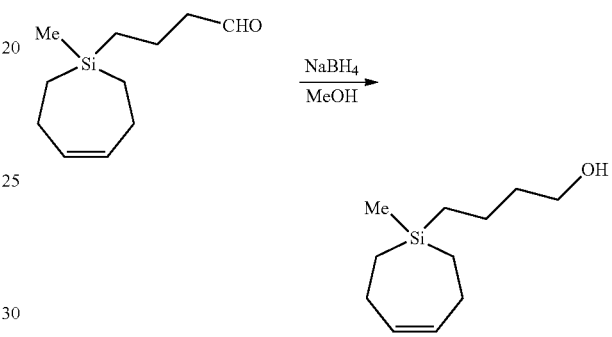

A 25 mL round-bottomed flask was charged with (Z)—Si-(4-Oxobutyl)-Si-methyl-5-silacycloheptene (422 mg, 2.15 mmol, 1.00 equiv) and methanol (11 mL). The flask was cooled by an ice bath (0° C.), and the mixture was magnetically stirred. Sodium borohydride (81.3 mg, 2.15 mmol, 1.00 equiv) was added slowly in small portions as a solid to the reaction mixture. The ice bath was removed, and the mixture was allowed to stir while warming to r.t. for 1 h. Water (3 mL) and 3M HCl (3 mL) were sequentially and cautiously added dropwise to the mixture. Methanol was removed by rotary evaporation, and the remainder was thrice extracted with diethyl ether. The combined organics were dried with anhydrous Na$_2$SO$_4$, filtered, and concentrated. Purification by flash column chromatography (5%-10% diethyl ether/hexane) afforded the title compound (403 mg, 2.03 mmol, 95% yield) as a colorless oil. $^1$H NMR (400 MHz, CDCl$_3$) δ: 5.80-5.73 (m, 2H), 3.65 (t, J=6.4 Hz, 2H), 2.23-2.19 (m, 4H), 1.63-1.56 (m, 2H), 1.41-1.33 (m, 2H), 1.24 (br s, 1H), 0.64-0.53 (m, 6H), 0.01 (s, 3H); $^{13}$C NMR (150 MHz, CDCl$_3$) δ: 132.7 (CH), 62.8 (CH$_2$), 36.8 (CH$_2$), 21.2 (CH$_2$), 20.0 (CH$_2$), 14.8 (CH$_2$), 12.8 (CH$_2$), −3.9 (CH$_3$).

Di(but-3-en-1-yl)diphenylsilane

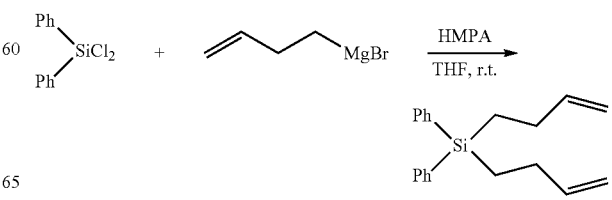

A dry round-bottomed flask was charged with Mg (2.85 g, 119 mmol, 3.50 equiv) and dry THF (200 mL) under nitrogen atmosphere. 4-Bromo-l-butene (12.3 mL, 121 mmol, 3.56 equiv) was introduced to the flask dropwise via syringe. The reaction mixture was allowed to stir at room temperature. After the formation of the Grignard reagent was judged complete, HMPA (29.6 mL, 170 mmol, 5.00 equiv) was added, followed by dichlorodiphenylsilane (7.15 mL, 34.0 mmol, 1.00 equiv). The reaction mixture was stirred at room temperature overnight. After reaction, THF was removed via rotary evaporation. Saturated aq. NH$_4$Cl (100 mL) and ethyl acetate (100 mL) were added and the aqueous layer was extracted three times with ethyl acetate. The organics were combined, dried with anhydrous MgSO$_4$, filtered, and concentrated via rotary evaporation. Purification by flash column chromatography (hexane) afforded the title compound as a colorless oil (7.03 g, 24.0 mmol, 71%). $^1$H NMR (400 MHz, CDCl$_3$) δ: 7.54-7.49 (m, 4H), 7.43-7.33 (m, 6H), 5.95-5.83 (m, 2H), 5.03-4.82 (m, 4H), 2.15-2.06 (m, 4H), 1.25-1.17 (m, 4H); $^{13}$C NMR (100 MHz, CDCl$_3$) δ: 141.4 (CH), 135.8 (C), 135.0 (CH), 129.4 (CH), 128.0 (CH), 113.1 (CH$_2$), 27.9 (CH$_2$), 11.8 (CH$_2$).

(Z)—Si—Si-diphenyl-5-sila-cycloheptene

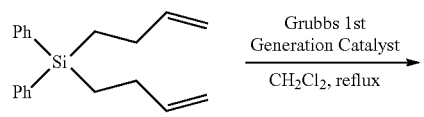

Di(but-3-en-1-yl)diphenylsilane (7.03 g, 24.0 mmol, 1.00 equiv) was dissolved in dry dichloromethane (120 mL). Grubbs 1$^{st}$ generation catalyst (594 mg, 0.722 mmol, 0.030 equiv) was added as a solution in dichloromethane (1.7 L) and the mixture was refluxed under nitrogen for 1 hour. The mixture was cooled to room temperature, and the reaction mixture was concentrated via rotary evaporation. Purification by flash column chromatography (hexane, R$_f$=0.6) afforded the title compound (4.50 g, 71% yield) as a colorless solid. $^1$H NMR (400 MHz, CDCl$_3$) δ: 7.56-7.50 (m, 4H), 7.41-7.32 (m, 6H), 5.90-5.82 (m, 2H), 2.40-2.30 (m, 4H), 1.29-1.22 (m, 4H); $^{13}$C NMR (100 MHz, CDCl$_3$) δ: 137.2 (CH), 134.7 (C), 132.7 (CH), 129.3 (CH), 128.0 (CH), 21.1 (CH$_2$), 11.4 (CH$_2$).

(3-Chloropropyl)(methyl)bis(2-methylallyl)silane

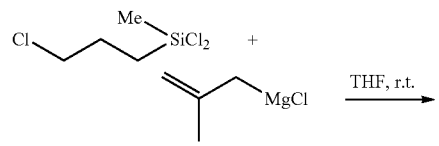

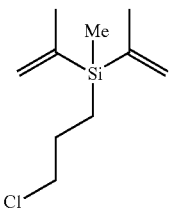

3-Methallylmagnesium chloride solution (12.5 mmol, 0.5M in THF, 2.5 equiv) was added under anhydrous conditions to a flame-dried round-bottomed flask. Then 3-chloropropyltrichlorosilane (958 mg, 5 mmol, 1.0 equiv) was added dropwise. The reaction was stirred for 6 h at room temperature. After reaction, THF was removed via rotary evaporation. Saturated NH$_4$Cl aqueous solution and diethyl ether were added, and aqueous layer was extracted with diethyl ether for 3 times. The collected organic layer was dried with anhydrous MgSO$_4$, filtered, and concentrated via rotary evaporation. Purification by flash column chromatography (n-hexane, R$_f$=0.6) afforded the desired (3-chloropropyl)(methyl)bis(2-methylallyl)silane as a colorless oil (950.4 mg, 83% yield).

3,3'-((3-chloropropyl)(methyl)silanediyl)bis(2-methylpropan-1-ol)

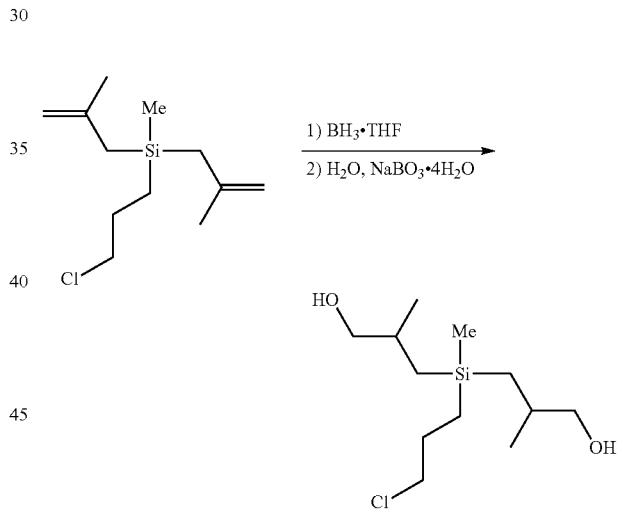

A 25 mL flame-dried round-bottomed flask was charged with (3-chloropropyl)(methyl)bis(2-methylallyl)silane (230 mg, 1.00 mmol, 1.00 equiv). The flask was cooled by an ice bath (0° C.). Borane THF complex solution (1.0 M in THF) (2.00 mL, 2.00 mmol, 2.00 equiv) was added dropwise to the reaction mixture. The ice bath was removed, and the mixture was allowed to stir while warming to r.t. for 3.5 h. Then 0.700 mL H$_2$O was added to the reaction at 0° C., followed by sodium perborate tetrahydrate (307 mg, 2.00 mmol, 2.00 equiv). The mixture was stirred at 40° C. for 12 h. After reaction, 10 mL brine solution and 10 mL ether was added, and aqueous layer was extracted with diethyl ether for 3 times. The collected organic layer was dried with anhydrous MgSO$_4$, filtered, and concentrated via rotary evaporation. Purification by flash column chromatography (30% Ethyl acetate/n-hexane) afforded the title compound as a colorless oil (172 mg, 63% yield).

3,3'-((3-chloropropyl)(methyl)silanediyl)bis(2-methylpropanal)

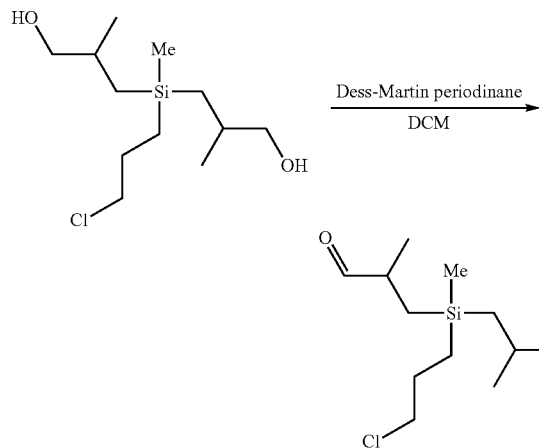

A 25 mL flame-dried round-bottomed flask was charged with (137 mg, 0.500 mmol, 1.00 equiv). Then Dess-Martin periodinane (636 mg, 1.50 mmol, 3.00 equiv) in 10 mL dry dichloromethane was added to the flask. The mixture was stirred at room temperature for 6 hours. After reaction, the insoluble solid was filtered out and rinsed with diethyl ether. The solution was combined and concentrated via rotary evaporation. Purification by flash column chromatography (1%-5% ethyl acetate/n-hexane) afforded the title compound as a colorless oil (114 mg, 85% yield).

(3-chloropropyl)(methyl)bis(2-methylbut-3-en-1-yl)silane

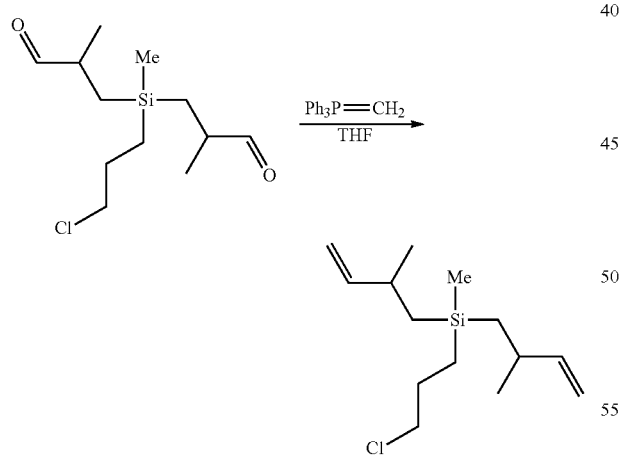

A solution of n-BuLi (1.6 M, 4.8 mL, 7.7 mmol, 2.5 equiv) in hexanes was added dropwise to a cooled (−78° C.) solution of methylphosphonium iodide (3.1 g, 7.7 mmol, 2.5 equiv) in THF (30 mL) and the mixture was allowed to warm to room temperature. After being cooled again to −78° C., a solution of 3,3'-((3-chloropropyl)(methyl)silanediyl)bis(2-methylpropanal) (811 mg, 3.1 mmol, 1.0 equiv) in THF (27 mL) was added. The reaction mixture was stirred for 30 min at −78° C. and at room temperature overnight. The reaction mixture was partitioned between dichloromethane and saturated solution of NH$_4$Cl. The organic layer was washed with brine, dried over MgSO$_4$, and concentrated. The crude residue was purified by flash chromatography (1% diethyl ether/hexane) to afford the title compound as a colorless oil (408 mg, 51% yield).

1-(3-chloropropyl)-1,3,6-trimethyl-2,3,6,7-tetrahydro-1H-silephine

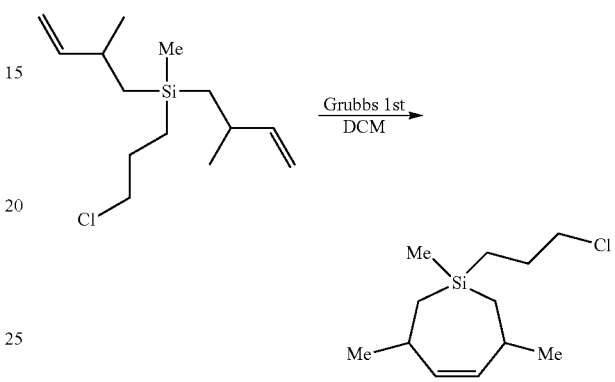

(3-chloropropyl)(methyl)bis(2-methylbut-3-en-1-yl)silane (389 mg, 1.5 mmol, 1.0 equiv) was dissolved in dry dichloromethane (144 mL). Grubbs 1$^{st}$ generation catalyst (61 mg, 0.074 mmol, 0.050 equiv) was added as a solution in dichloromethane (10 mL) and the mixture was refluxed under nitrogen for 4 hours. The mixture was cooled to room temperature, and the reaction mixture was concentrated via rotary evaporation. Purification by flash column chromatography (hexane) afforded the title compound (341 mg, 98% yield) as a colorless oil.

3-(1,3,6-trimethyl-2,3,6,7-tetrahydro-1H-silepin-1-yl)propyl acetate

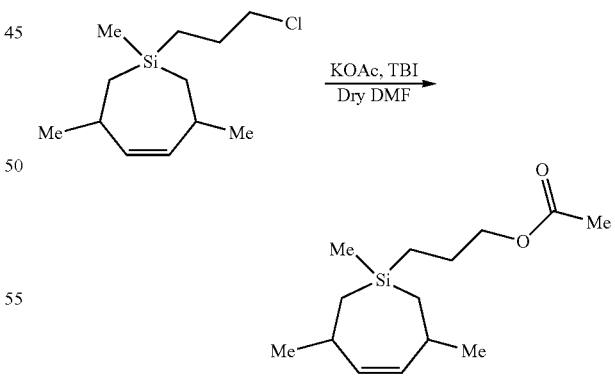

A 10 mL flame-dried round-bottomed flask was charged with KOAc (98 mg, 1.0 mmol, 2.0 equiv) and Tetrabutylammonium iodide (9.2 mg, 0.025 mmol, 0.050 equiv). Then a solution of 1-(3-chloropropyl)-1,3,6-trimethyl-2,3,6,7-tetrahydro-1H-silephine (116 mg, 0.5 mmol, 1.0 equiv) in dry DMF (1 mL) was added to the mixture. The reaction was heated up to 100° C. and stirred overnight. After the reaction, 10 mL brine solution and 10 mL ether was added. The ether layer was washed with water to remove DMF. The organic layer was dried over MgSO$_4$ and concentrated. The crude residue was purified by flash chromatography (1% diethyl ether/hexane) to afford 3-(1,3,6-trimethyl-2,3,6,7-tetrahydro-1H-silepin-1-yl)propyl acetate as a colorless oil (122 mg, 96% yield).

3-(1, 3, 6-trimethyl-2,3,6,7-tetrahydro-1H-silepin-1-yl)propan-1-ol

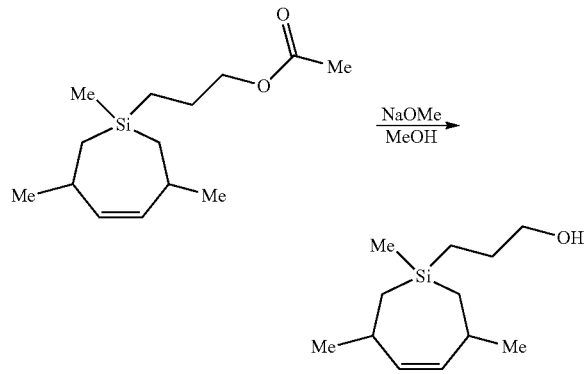

A 10 mL round-bottomed flask was charged with sodium methoxide (2.2 mg, 0.041 mmol, 0.1 equiv). A solution of 3-(1,3,6-trimethyl-2,3,6,7-tetrahydro-1H-silepin-1-yl)propyl acetate (105 mg, 0.41 mmol, 1.0 equiv) in MeOH (4 mL) was added. The reaction mixture was allowed to stir at room temperature overnight. After the reaction, 10 mL brine solution and 10 mL ether was added, and aqueous layer was extracted with diethyl ether for 3 times. The collected organic layer was dried with anhydrous MgSO$_4$, filtered, and concentrated via rotary evaporation. Purification by flash column chromatography (30% diethyl ether/n-hexane) afforded the desired 3-(1,3,6-trimethyl-2,3,6,7-tetrahydro-1H-silepin-1-yl)propan-1-ol as a colorless oil (82 mg, 94% yield).

General Procedure for Photoisomerization of Trans-Cycloheptene Derivatives

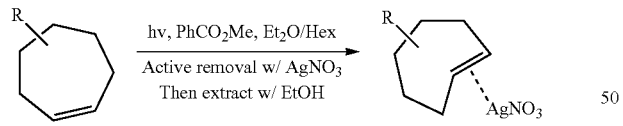

The cis-cycloheptene derivative and methyl benzoate (1.43 g, 10.4 mmol, 2.0 equiv) were dissolved in 500 mL of solvent in a round-bottomed flask. The round-bottomed flask was immersed in a cooling bath (NESLAB CB 80 with a CRYOTROL controller, bath temperature was set to −40° C.) and connected via PTFE tubing successively to an FMI "Q" pump, a three-way tee that was equipped with a thermometer probe, a coil of FEP tubing (total length: 1 m; ID: 1/16 inch; OD 1/8 inch) and a 25 g Biotage® column as illustrated in FIG. 1. The FEP tubing coil was placed in a Rayonet® RPR-100 reactor. The bottom of the column was packed with dry silica gel (6 cm), and the top of the column was packed with silver nitrate impregnated silica (10 wt % of AgNO$_3$, 11.5 g, 1.30 equiv). The column was flushed with 200 mL of the reaction solvent. The pump was turned on and the rate of circulation was adjusted to approx. 100 mL per minute. The temperature at the three-way tee was maintained at 0° C. The lamp was then turned on, and photoisomerization of the stirring mixture was carried out for the indicated time. Afterwards, the sensitizer was flushed from the column with 400 mL of 20% ether in hexanes. The column was then dried by a stream of compressed air, and then flushed with ethanol. The trans-cycloheptene silver (I) complex was collected and stored in a freezer as a solution in ethanol (200 mL).

trans-Cycloheptene.AgNO$_3$

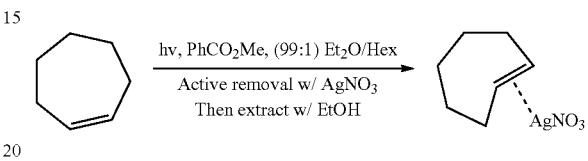

The general photoisomerization procedure was followed using cis-cycloheptene (500 mg, 5.21 mmol) and 1:99 ether:hexanes as solvent. The flow-photoisomerization reaction was carried out for 6 hours to provide 984 mg (71% yield) of the title compound in ethanol solution.

(4E)-Cyclohept-4-en-1-ol.AgNO$_3$

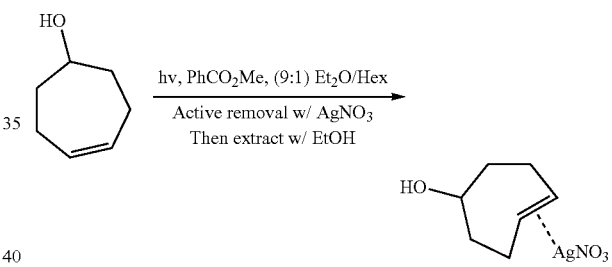

The general photoisomerization procedure was followed by using (4E)-cyclohept-4-en-1-ol (500 mg, 4.46 mmol) and 9:1 ether:hexanes as solvent. The flow-photoisomerization reaction was carried out for 8 hours to provide 919 mg (73% yield) of the title compound in ethanol solution.

(4E)-Cyclohept-4-en-1-ylmethanol.AgNO$_3$

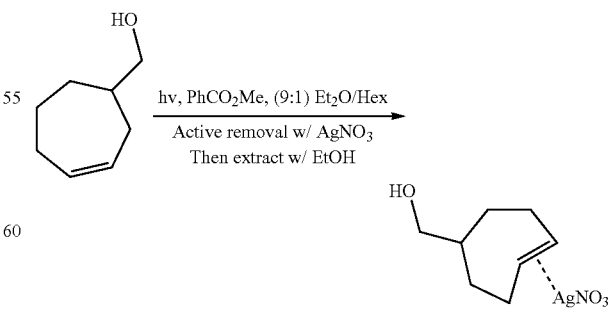

The general photoisomerization procedure was followed by using (4Z)-cyclohept-4-en-1-ylmethanol (200 mg, 1.59 mmol) and 9:1 ether:hexanes as solvent. The flow-photoisomerization reaction was carried out for 8 hours to provide 282 mg (60% yield) of the title compound in ethanol solution.

rel-(1R, 3E, pR)-Cyclohept-3-en-1-ol.AgNO₃ Complex and rel-(1R, 3E, pS)-Cyclohept-3-en-1-ol.AgNO₃

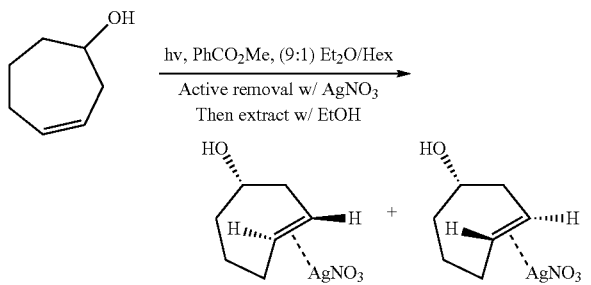

The general photoisomerization procedure was followed using (3Z)-Cyclohept-3-en-1-ol (62 mg, 0.554 mmol) and 9:1 ether:hexanes as solvent. The flow-photoisomerization reaction was carried out for 4 hours to provide 84 mg (54% yield) of the title compounds in ethanol solution.

rel-(1R, 2E)-Cyclohept-3-en-1-ol.AgNO₃ Complex

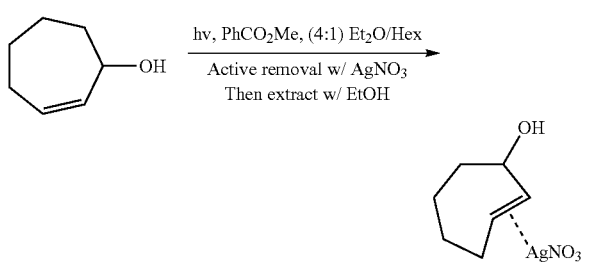

The general photoisomerization procedure was followed by using (2Z) cyclohept-2-en-1-ol (200 mg, 1.59 mmol, prepared according to the method of Huber, R. S. et al., *J. Org. Chem.* 1992, 57, 5778) and 9:1 ether:hexanes as solvent. The flow-photoisomerization reaction was carried out for 6 hours to provide 238 mg (50% yield) of the title compound in ethanol solution.

rel-(1S, 2S, 3E, pR)-cyclohept-3-ene-1,2-diol.AgNO₃ and rel-(1S, 2S, 3E, pS)-cyclohept-3-ene-1,2-diol.AgNO₃

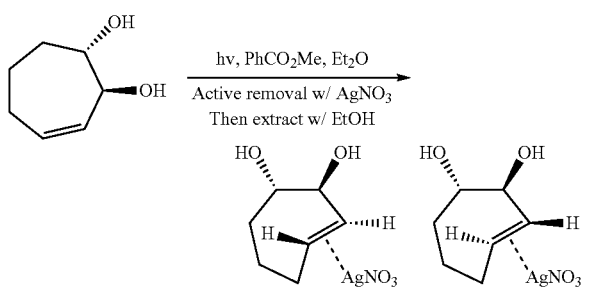

The general photoisomerization procedure was followed by using (1S,2S)-cyclohept-3-ene-1,2-diol (200 mg, 1.56 mmol) and ether as solvent. The flow-photoisomerization was carried out for 8 hours to provide 233 mg (50% yield) of the title compounds in ethanol solution.

(4E)-tert-Butyl-2,3,6,7-tetrahydro-1H-azepine-1-carboxylate.AgNO₃

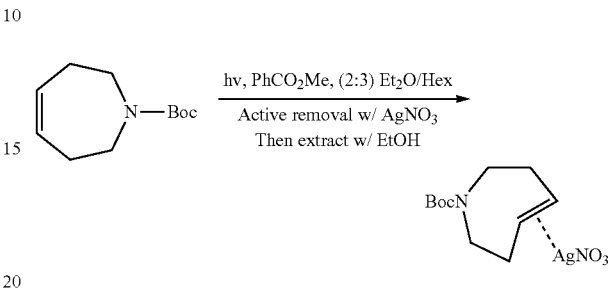

The general photoisomerization procedure was followed by using (4Z)-tert-Butyl 2,3,6,7-tetrahydro-1H-azepine-1-carboxylate (133 mg, 0.675 mmol) and 2:3 ether:hexanes as solvent. The flow-photoisomerization reaction was carried out for 3 hours to provide 119 mg (48% yield) of the title compound in ethanol solution.

(4E)-Cyclohept-4-en-1-one.AgNO₃

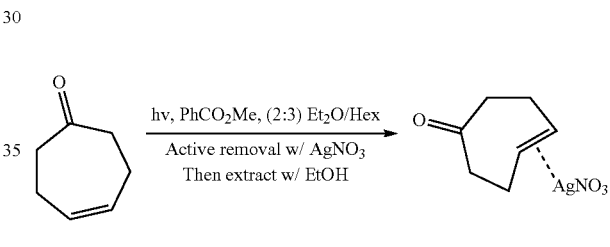

The general photoisomerization procedure was followed by using (4)-Cyclohept-4-en-1-one (100 mg, 0.909 mmol) and 2:3 ether:hexanes as solvent. The flow-photoisomerization reaction was carried out for 5 hours to provide 50% of the title compound in ethanol solution.

Photoisomerization of Silicon-Containing Trans-Cycloheptene Derivatives

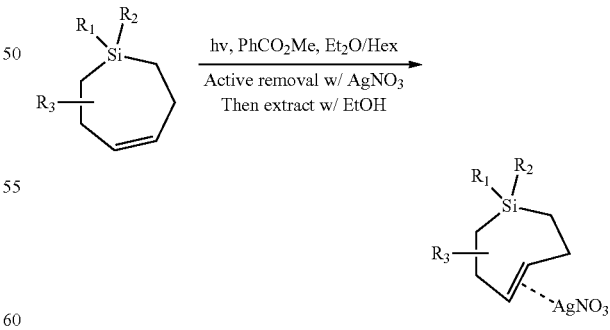

The (Z)-sila-cycloheptene derivative (100 mg) and methyl benzoate (2.0 equiv) were dissolved in 100 mL of solvent in a quartz flask into which $N_2$ was sparged. The quartz flask was placed in a Rayonet® reactor and connected via PTFE tubing to a column (Biotage® SNAP cartridge, 10 g) and an FMI pump. The bottom of the column was packed with dry silica gel, and the top of the column was packed with silver nitrate impregnated silica (2.0 equiv). The column was flushed with 7:3 hexane:ether. The pump was turned on and the rate of circulation was adjusted to about 100 mL per minute. The lamp was then turned on, and photolysis of the mixture was carried out for the indicated time. The column was washed with additional solvent (100 mL) and then dried by a stream of compressed air. The SNAP cartridge was then flushed with 150 mL of EtOH to afford an ethanol solution of (E)-sila-cycloheptene.AgNO$_3$ derivative. The ethanol solution was concentrated via rotary evaporation, affording the corresponding (E)-sila-cycloheptene.AgNO$_3$ derivative and free AgNO$_3$. The NMR yield of the trans-cycloheptene.AgNO$_3$ complex was determined by comparing the integration of the trans-alkene protons to mesitylene (1.0 equiv) that was added as an NMR standard.

(E)-Si-(3-cyanopropyl)-Si-methyl-5-silacycloheptene.AgNO$_3$

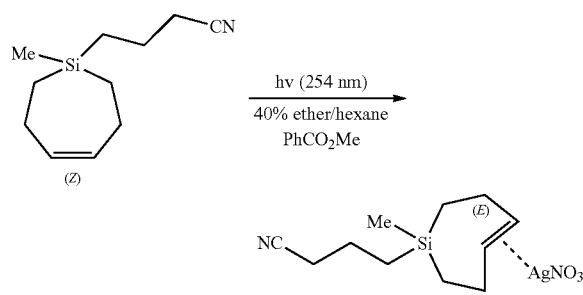

(Z)—Si-(3-cyanopropyl)-Si-methyl-5-silacycloheptene (100 mg, 0.517 mmol, 1.00 equiv) and methyl benzoate (145 mg, 1.06 mmol, 2.05 equiv) were placed in a quartz flask and dissolved in 100 mL of 2:3 Et$_2$O:hexanes that had been degassed through three freeze/pump/thaw cycles. Dodecane (87 mg, 0.51 mmol, 1.0 equiv) was added to the flask to allow for GC monitoring. The solution in the quartz flask was then irradiated (254 nm) under continuous flow conditions (100 mL/min) for 3 hours with N$_2$ sparging, at which point GC analysis indicated that the reaction was complete. The SNAP cartridge was flushed with 200 mL of 1:4 Et$_2$O/hexanes and then dried with compressed air. The SNAP cartridge was then flushed with 225 mL of EtOH to afford an ethanol solution of (E)-Si-(3-Cyanopropyl)-Si-methyl-5-silacycloheptene.AgNO$_3$. The ethanol solution was concentrated via rotary evaporation, affording a dark brown viscous oil consisting of trans-cycloheptene.AgNO$_3$ complex (0.398 mmol by NMR analysis, 77% yield) and free AgNO$_3$.

(E)-Si-(4-hydroxybutyl)-Si-methyl-5-silacycloheptene.AgNO$_3$

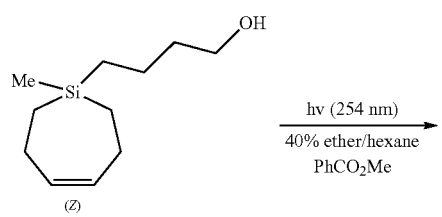

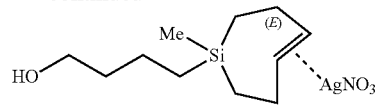

(Z)—Si-(4-hydroxybutyl)-Si-methyl-5-silacycloheptene (100 mg, 0.510 mmol, 1.00 equiv) and methyl benzoate (138 mg, 1.02 mmol, 2.00 equiv) were placed in a quartz flask and dissolved in 100 mL of 2:3 Et$_2$O:hexanes that had been degassed through three freeze/pump/thaw cycles. Dodecane (86 mg, 0.51 mmol, 1.0 equiv) was added to the flask to allow for GC monitoring. The solution in the quartz flask was then irradiated (254 nm) under continuous flow conditions (100 mL/min) for 3 hours with N$_2$ sparging, at which point GC analysis indicated that the reaction was complete. The SNAP cartridge was flushed with 200 mL of 1:4 Et$_2$O/hexanes and then dried with compressed air. The SNAP cartridge was then flushed with 225 mL of EtOH to afford an ethanol solution of (E)-Si-(4-hydroxybutyl)-Si-methyl-5-silacycloheptene.AgNO$_3$. The ethanol solution was concentrated via rotary evaporation, affording a tan viscous oil consisting of trans-cycloheptene.AgNO$_3$ complex (0.377 mmol by NMR analysis, 74% yield) and free AgNO$_3$.

(E)-Si, Si-diphenyl-5-silacycloheptene.AgNO$_3$

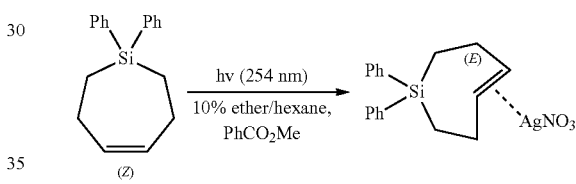

(Z)—Si, Si-diphenyl-5-silacycloheptene (100 mg, 0.379 mmol, 1.00 equiv) and methyl benzoate (517 mg, 3.77 mmol, 10.0 equiv) were placed in a quartz flask and dissolved in 100 mL of 1:9 Et$_2$O:hexanes that had been degassed through three freeze/pump/thaw cycles. Dodecane (64.7 mg, 0.380 mmol, 1.00 equiv) was added to the flask to allow for GC monitoring. The solution in the quartz flask was then irradiated (254 nm) under continuous flow conditions (100 mL/min) for 6 hours with N$_2$ sparging, at which point GC analysis indicated that the reaction was complete. The SNAP cartridge was flushed with 100 mL of 1:5 Et$_2$O/hexanes and then dried with compressed air. The SNAP cartridge was then flushed with 100 mL of EtOH to afford an ethanol solution of (E)-Si, Si-diphenyl-5-silacycloheptene.AgNO$_3$. The ethanol solution was concentrated via rotary evaporation, affording a dark brown viscous oil consisting of trans-cycloheptene.AgNO$_3$ complex (0.201 mmol by NMR analysis, 53% yield) and free AgNO$_3$.

(E)-1,1-dimethyl-2,3,6,7-tetrahydro-1H-silepin-3-ol.AgNO$_3$

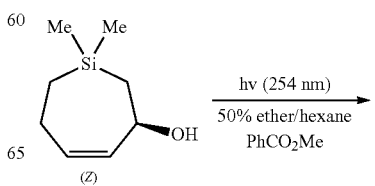

-continued

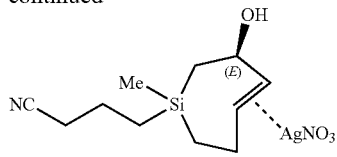

(Z)-1,1-dimethyl-2,3,6,7-tetrahydro-1H-silepin-3-ol (100 mg, 0.640 mmol, 1.00 equiv) and methyl benzoate (174.2 mg, 1.28 mmol, 2.00 equiv) were placed in a quartz flask and dissolved in 100 mL of 1:1 Et$_2$O:hexanes that had been degassed through three freeze/pump/thaw cycles. Dodecane (109 mg, 0.640 mmol, 1.00 equiv) was added to the flask to allow for GC monitoring. The solution in the quartz flask was then irradiated (254 nm) under continuous flow conditions (100 mL/min) for 1 hour with N$_2$ sparging, at which point GC analysis indicated that the reaction was complete. The SNAP cartridge was flushed with 100 mL of 1:5 Et$_2$O/hexanes and then dried with compressed air. The SNAP cartridge was then flushed with 100 mL of EtOH to afford an ethanol solution of (E)-Si, Si-diphenyl-5-silacycloheptene.AgNO$_3$. The ethanol solution was concentrated via rotary evaporation, affording a brown viscous oil consisting of trans-cycloheptene.AgNO$_3$ complex (0.525 mmol by NMR analysis, 82% yield) and free AgNO$_3$.

(E)-3-(1,3,6-trimethyl-2,3,6,7-tetrahydro-1H-silepin-1-yl)propan-1-ol.AgNO$_3$

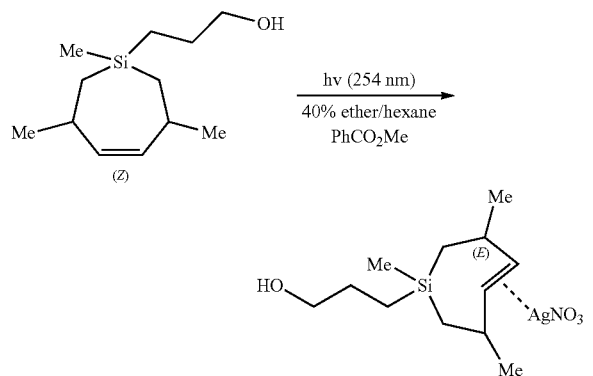

(Z)-3-(1,3,6-trimethyl-2,3,6,7-tetrahydro-1H-silepin-1-yl)propan-1-ol (101 mg, 0.470 mmol, 1.00 equiv) and methyl benzoate (323 mg, 2.35 mmol, 5.00 equiv) were placed in a quartz flask and dissolved in 100 mL of 2:3 Et$_2$O:hexanes that had been degassed through three freeze/pump/thaw cycles. Dodecane (80.0 mg, 0.470 mmol, 1.00 equiv) was added to the flask to allow for GC monitoring. The solution in the quartz flask was then irradiated (254 nm) under continuous flow conditions (100 mL/min) for 6 hours with N$_2$ sparging, at which point GC analysis indicated that the reaction was complete. The SNAP cartridge was flushed with 100 mL of 1:4 Et$_2$O/hexanes and then dried with compressed air. The SNAP cartridge was then flushed with 150 mL of EtOH to afford an ethanol solution of (E)-3-(1,3,6-trimethyl-2,3,6,7-tetrahydro-1H-silepin-1-yl)propan-1-ol.AgNO$_3$. The ethanol solution was concentrated via rotary evaporation, affording a tan viscous oil consisting of trans-cycloheptene.AgNO$_3$ complex (0.320 mmol by NMR analysis, 68% yield) and free AgNO$_3$.

Reactions of Trans-Cycloheptene.AgNO$_3$ Complexes 1,4-Diphenyl-6,7,8,9-tetrahydro-5H-cyclohepta[d]pyridazine

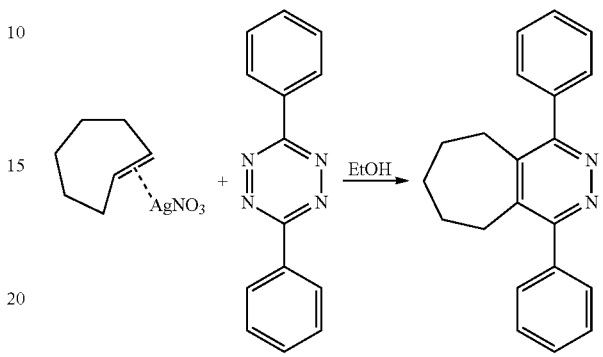

3,6-diphenyl-s-tetrazine (234 mg, 1.00 mmol) in 10 mL dichloromethane was added to a ethanolic solution of trans-cycloheptene.AgNO$_3$ (60.0 mL of a 13.9 mM solution in EtOH, 0.833 mmol) with stirring at room temperature. Nitrogen evolved immediately upon mixing and a black precipitate was formed. After stirring for 30 minutes, the reaction mixture was filtered and the filtrate was concentrated down onto silica gel using a rotary evaporator and loaded onto a flash column. Column chromatography using a gradient (0-50%) of ethyl acetate in hexanes followed by 5% methanol in dichloromethane as eluents afforded the title product (246 mg, 0.820 mmol, 98%) as a white solid. $^1$H NMR (600 MHz, CDCl$_3$, δ): 7.48-7.42 (m, 10H), 2.83-2.78 (m, 4H), 1.93-1.86 (m, 2H), 1.72-1.62 (m, 4H). $^{13}$C NMR (CDCl$_3$, 100 MHz, δ): 161.5 (u, 2C), 145.8 (u, 2C), 137.0 (u, 2C), 130.0 (d, 2C), 129.4 (d, 2C), 128.4 (d, 2C), 31.9 (u, 2C), 31.2 (u, 1C), 25.8 (u, 2C).

rel-(1R,2R)-Cycloheptane-1,2-diol

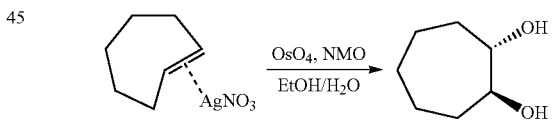

N-Methylmorpholine N-oxide monohydrate (115 mg, 0.852 mmol) and 4 wt % OsO$_4$ in aqueous solution (125 μL, 20.5 μmol) were sequentially added to an ethanolic solution of trans-cycloheptene.AgNO$_3$ (50.0 mL of a 13.1 mM solution in EtOH, 0.654 mmol) The resulting mixture was allowed to stir for 2 hours at room temperature. The mixture was diluted with saturated NaHSO$_3$ aqueous solution (50 mL) and filtered, and filtrate was extracted with ethyl acetate (8×25.0 mL), and the organics were combined, dried over MgSO$_4$ and concentrated by rotary evaporation. Purification by column chromatography with a gradient (0-5%) of methanol in dichloromethane afforded the title compound (70.0 mg, 0.538 mmol, 82%) as a pale yellow solid, mp 53-54° C. $^1$H NMR (600 MHz, CDCl$_3$, δ): 3.45-3.40 (m, 2H), 2.61 (br s, 2H), 1.90-1.85 (m, 2H), 1.70-1.62 (m, 2H), 1.55-1.42 (m, 6H). $^{13}$C NMR (CDCl$_3$, 100 MHz, δ): 78.1 (d, 2C), 32.5 (u, 2C), 26.5 (u, 1C), 22.2 (d, 2C).

rel-(1R,4S,4aR,9aR)-4,4a,5,6,7,8,9,9a-Octahydro-1H-1,4-methanobenzo[7]annulene

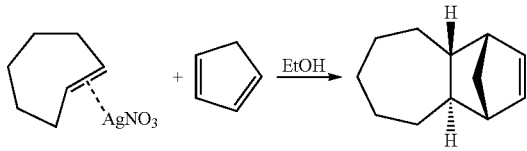

Freshly cracked cyclopentadiene (412 mg, 6.24 mmol) was added to a 12.5 mM ethanol solution that contains trans-cycloheptene silver (I) nitrate complex (50.0 mL, 0.624 mmol). The mixture was allowed to stir at room temperature overnight. The reaction mixture was then filtered and concentrated down using rotary evaporator. Purification by column chromatography using hexane afforded title product (83.0 mg, 0.512 mmol, 82%) as a clear oil. $^1$H NMR (400 MHz, CDCl$_3$, δ): 6.23 (dd, J=5.8, 3.0 Hz, 1H), 5.90 (dd, J=5.7, 2.9 Hz, 1H), 2.61 (m, 1H), 2.34 (m, 1H), 1.85-1.40 (m, 10H), 1.40-1.33 (m, 1H), 1.30-1.17 (m, 1H), 1.00-0.92 (m, 1H), 0.83-0.72 (m, 1H). $^{13}$C NMR (CDCl$_3$, 100 MHz, δ): 139.1 (d, 1C), 131.7 (d, 1C), 47.5 (d, 1C), 47.3 (u, 1C), 47.2 (d, 1C), 45.3 (d, 1C), 44.9 (d, 1C), 32.8 (u, 1C), 30.8 (u, 1C), 29.5 (u, 1C), 29.3 (u, 1C), 25.1 (u, 1C).

Reactions of (E)-Si, Si-Diphenyl-5-silacycloheptene

6,6-diphenyl-3,3a,4,5,6,7,8,8a-octahydrosilepino[4,5-c]pyrazole

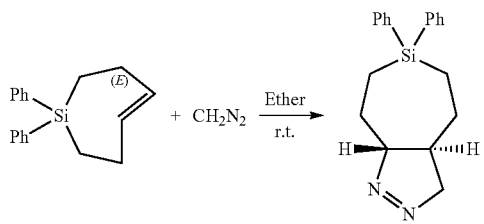

(E)-Si, Si-Diphenyl-5-silacycloheptene.AgNO$_3$ (0.19 mmol, 1.0 equiv) was suspended in ethyl ether (10 mL) and saturated brine (10 mL). The aqueous layer was extracted with ether (3×10 mL). The organics were combined, dried with anhydrous Na$_2$SO$_4$ and filtered. Diazald (325 mg, 1.52 mmol) was taken up in 30 mL of absolute ethanol in a Lombardi flask. Behind a blast shield, KOH (426 mg, 7.6 mmol) in 1.2 mL of water was added dropwise, and the resulting diazomethane was bubbled into the flask containing the sila-trans-cycloheptene using a stream of nitrogen. After the diazomethane solution had changed from yellow to colorless, nitrogen was bubbled for an additional 15 min. The ether solution was concentrated via rotary evaporation, and the residue was purified by flash column chromatography (5% ethyl acetate/hexane) to afford the title compound (37.7 mg, 65% yield) as a colorless oil. $^1$H NMR (600 MHz, CDCl$_3$) δ: 7.53-7.52 (m, 2H), 7.48-7.46 (m, 2H), 7.41-7.34 (m, 6H), 4.86 (ddd, J=17.5, 9.3, 2.5 Hz, 1H), 3.81 (m, 1H), 3.70 (ddd, J=17.5, 9.6, 3.0 Hz, 1H), 3.20 (dtd, J=10.8, 7.0, 3.8 Hz, 1H), 2.25-2.20 (m, 1H), 1.70-1.60 (m, 2H), 1.51-1.42 (m, 4H), 1.34-1.29 (m, 2H); $^{13}$C NMR (100 MHz, CDCl$_3$) δ: 136.7 (C), 136.2 (C), 134.2 (CH), 134.1 (CH), 129.6 (CH), 129.5 (CH), 128.3 (CH), 128.2 (CH), 93.8 (CH), 83.2 (CH$_2$), 40.6 (CH), 27.2 (CH$_2$), 26.9 (CH$_2$), 12.7 (CH$_2$), 9.6 (CH$_2$).

(rel-1R,7R)-9,9-dichloro-4,4-diphenyl-4-silabicyclo[5.2.0]nonan-8-one

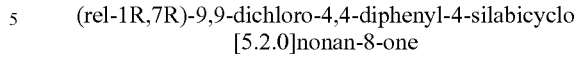

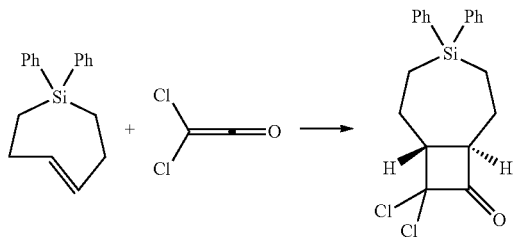

In a round-bottomed flask, (E)-Si, Si-diphenyl-5-silacycloheptene.AgNO$_3$ (0.29 mmol, 1.0 equiv) was combined with dichloromethane (2 mL) and conc. ammonium hydroxide (2 mL). The aqueous layer was extracted twice with dichloromethane, and the organics were combined and dried over Na$_2$SO$_4$. The organic solution was purified through a plug of silica gel (4 cm high×2 cm diameter) eluting with CH$_2$Cl$_2$. Without evaporating to dryness, the eluate was concentrated to an approximate volume of 1 mL. The solution was added to a separate flask that had been charged with dichloromethane (1 mL) and triethylamine (1.27 mmol, 177.1 µl, 4.4 equiv) under an N$_2$ atmosphere. Dichloroacetyl chloride (1.15 mmol, 111 µL, 4.0× equiv) in dichloromethane (1 mL) was then added dropwise at room temperature, and the resulting mixture was allowed to stir at room temperature for 2 hours. The mixture was washed with sat. aq. NaHCO$_3$ (10 mL), and the aqueous layer was extracted with dichloromethane (140 mL). The organics were combined, dried, and purified by flash column chromatography (30% diethyl ether/hexane) to afford the title compound (83.9 mg, 78% yield) as a yellow solid. $^1$H NMR (600 MHz, CDCl$_3$) δ: 7.51-7.50 (m, 2H), 7.44-7.34 (m, 8), 3.29-3.24 (m, 1H), 2.57-2.47 (m, 2H), 2.29-2.23 (m, 1H), 2.01-1.94 (m, 1H), 1.94-1.87 (m, 1H), 1.62 (dt, J=14.8, 5.6 Hz, 1H), 1.45-1.32 (m, 3H); $^{13}$C NMR (150 MHz, CDCl$_3$) δ: 195.1 (C), 136.1 (C), 135.3 (C), 134.2 (CH), 134.1 (CH), 129.9 (CH), 129.8 (CH), 128.6 (CH), 128.3 (CH), 86.9 (C), 62.3 (CH), 53.8 (CH), 24.4 (CH$_2$), 21.6 (CH$_2$), 11.3 (CH$_2$), 10.7 (CH$_2$).

(3aR,8aR)-1-benzyl-6,6-diphenyl-1,3a,4,5,6,7,8,8a-octahydrosilepino[4,5-d][1,2,3]triazole

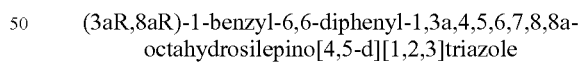

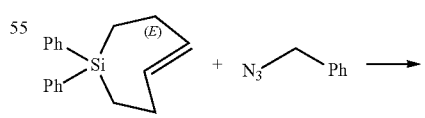

In a round-bottomed flask, (E)-Si, Si-diphenyl-5-silacycloheptene.AgNO₃ (0.43 mmol, 1.0 equiv) was combined with dichloromethane (2 mL) and conc. ammonium hydroxide (2 mL). The aqueous layer was extracted twice with dichloromethane, and the organics were combined and dried over Na₂SO₄. The organic solution was purified through a plug of silica gel (4 cm high×2 cm diameter) eluting with CH₂Cl₂. Without evaporating to dryness, the eluate was concentrated to an approximate volume of 1 mL. The solution was transferred into a 10 mL flask with the assistance of 3 mL of anhydrous dichloromethane. Benzyl azide (1.72 mmol, 227 µL) was then added to the dichloromethane solution. The mixture was stirred at room temperature for 30 min. The dichloromethane solution was concentrated via rotary evaporation, and the residue was purified on silica gel that was first deactivated with 10% triethylamine/hexane. Flash chromatography (15% diethyl ether/hexane, $R_f$=0) afforded the title compound (195 mg, 90% yield) as a white solid, mp 108-110° C. ¹H NMR (600 MHz, DMSO-d₆) δ: 7.48-7.30 (m, 8H), 7.26-7.24 (m, 3H), 7.11-7.09 (m, 2H), 4.7 (d, J=15.0 Hz, 1H), 4.42 (d, J=15.0 Hz, 1H), 3.71-3.66 (m, 1H), 2.65-2.61 (m, 2H), 2.30 (ddd, J=13.0, 10.4, 6.7 Hz, 1H), 1.50-1.43 (m, 1H), 1.41-1.36 (m, 1H), 1.34-1.27 (m, 3H), 1.21 (dt, J=15.3, 7.7 Hz, 1H); ¹³C NMR (150 MHz, DMSO-d₆) δ: 136.5 (C), 136.1 (C), 136.0 (C), 133.8 (CH), 133.7 (CH), 129.32 (CH), 129.27 (CH), 128.44 (CH), 128.37 (CH), 128.09 (CH), 128.05 (CH), 127.38 (CH), 83.9 (CH), 64.3 (CH), 52.2 (CH₂), 27.1 (CH₂), 25.6 (CH₂), 8.1 (CH₂), 8.0 (CH₂).

(5aR,9aR)-3,3-diphenyl-2,3,4,5,5a,6,9,9a-octahydro-1H-6,9-methanobenzo[d]silepine

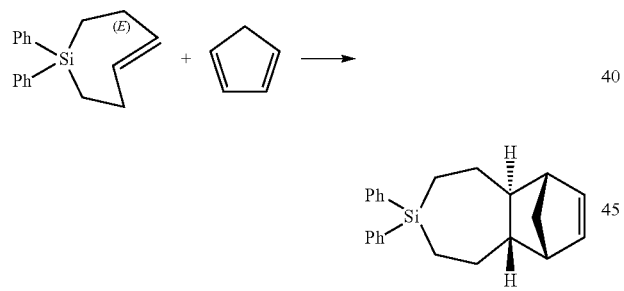

(E)-Si, Si-Diphenyl-5-silacycloheptene.AgNO₃ (51.0 mg in ethanol, 0.12 mmol, 1.0 equiv) was concentrated by rotary evaporation and immediately suspended in dichloromethane (5 mL) and saturated brine (5 mL). The precipitate was filtered and the aqueous layer was extracted with dichloromethane. The organics were dried with anhydrous MgSO₄ and filtered.

Then freshly cracked cyclopentadiene (78.0 mg, 1.18 mmol, 10.0 equiv) was added to this dichloromethane solution of (E)-Si, Si-Diphenyl-5-silacycloheptene. The mixture was allowed to stir at room temperature for 1 hour. After reaction, the dichloromethane solution was concentrated via rotary evaporation, the residue was purified by flash column chromatography to afford the title compound as a colorless oil.

Fleming-Tamao Oxidation rel-2,2'-((1R,2S,3S,4S)-bicyclo[2.2.1]hept-5-ene-2,3-diyl)bis(ethan-1-ol)

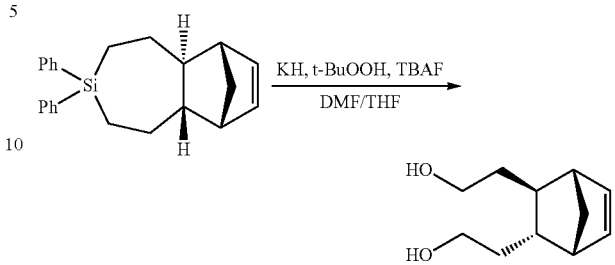

Potassium hydride (494 mg, 6.18 mmol, purchased as a suspension in mineral oil and rinsed with hexane prior to use) was suspended in DMF (3 mL), and the flask cooled by an ice bath (0° C.). tert-Butyl hydroperoxide (1.13 mL, 5.5 M in decane, 6.2 mmol) was added dropwise. The mixture was allowed to warm to room temperature. rel-(5aS,6R,9S,9aS)-3,3-diphenyl-2,3,4,5,5a,6,9,9a-octahydro-1H-6,9-methanobenzo[d]silepine (170 mg, 0.515 mmol) in anhydrous DMF (4 mL) was added to the mixture dropwise. After 10 min, n-Bu₄NF solution (1.0 M in THF, 2.10 mL, 2.10 mmol) was added. The reaction was heated at 70° C. overnight. After the mixture was cooled to room temperature, excessive amount of sodium thiosulfate pentahydrate (3.00 g, 12.1 mmol) was added. After stirring for 30 min, the resulting mixture was filtered and solvent was removed by rotary evaporator. The solid residue was dissolved by dichloromethane and the resulting solution was filtered, and concentrated by rotary evaporation. Purification by column chromatography with a gradient (30%-100%) of ethyl acetate in hexanes yielded title compound (71.4 mg, 0.396 mmol, 76%) as a white solid, mp 61-63° C. ¹H NMR (600 MHz, CDCl₃, δ): 6.18 (dd, J=5.8, 3.1 Hz, 1H), 5.99 (dd, J=5.8, 2.9 Hz, 1H), 3.80-2.60 (m, 4H), 2.73 (s, 1H), 2.49 (s, 1H), 1.92 (brs, 2H), 1.76-1.62 (m, 3H), 1.49-1.36 (m, 4H), 1.06-1.02 (m, 1H). ¹³C NMR (CDCl₃, 100 MHz, δ): 137.8 (d, 1C), 133.8 (d, 1C), 62.31 (u, 1C), 63.28 (u, 1C), 47.4 (d, 1C), 46.5 (u, 1C), 45.9 (d, 1C), 43.5 (d, 1C), 42.4 (d, 1C), 39.3 (u, 1C), 37.8 (u, 1C).

Preparation of (E)-Si-(3-Cyanopropyl)-Si-Methyl-5-sila-cycloheptene Derivatives (E) 4-(1-methyl-2,3,6,7-tetrahydro-1H-silepin-1-yl)butyl(4-nitrophenyl)carbonate.AgNO₃

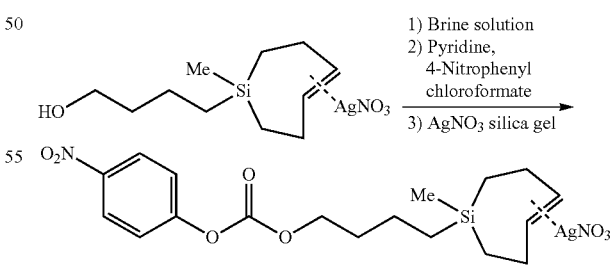

To a solution of (E)-Si-(4-hydroxybutyl)-Si-Methyl-5-silacycloheptene.AgNO₃ (51.0 mg in ethanol, 0.19 mmol, 1.0 equiv) was added dichloromethane (5 mL) followed by saturated brine (5 mL). The aqueous layer was extracted with dichloromethane (2×5 mL). The organics were dried with anhydrous MgSO₄ and filtered. This dichloromethane solution was transferred to a 50 mL round-bottomed flask, and pyridine (37.6 mg, 0.48 mmol, 2.5 equiv) and a solution of 4-nitrophenyl chloroformate (201.6 mg, 0.29 mmol, 1.5 equiv) in dichloromethane (1 mL) were sequentially added dropwise by syringe.

The mixture was allowed to stir for 0.5 h at room temperature. The mixture was directly loaded onto silica gel column. Flash chromatography (diethyl ether/hexane, $R_f=$) afforded the title compound as a solution in diethyl ether/hexane. The solution was combined and loaded onto a plug of 646 mg silica gel (impregnated with 10% w/w $AgNO_3$), which was packed in an 11 g Biotage® SNAP cartridges (contained a bed of unmodified silica gel). The silica gel was flushed with 15% diethyl ether/hexane (100 mL) for 2 h with a FMI pump. After the complexation, the silica gel was then flushed with 30% ether/hexane (100 mL) and then dried with compressed air. The SNAP cartridge was then flushed with EtOH (100 mL) to afford an ethanol solution of the title compound. The ethanol solution was concentrated via rotary evaporation, affording a viscous white oil that contained the title silver complex (22% NMR yield) in a mixture with $AgNO_3$. $^1$H NMR (600 MHz, MeOD) δ: 8.31 (d, J=9.1 Hz, 2H), 7.46 (d, J=9.1 Hz, 2H), 5.59-5.56 (m, 2H), 4.30 (t, J=6.4 Hz, 2H), 2.54 (ddd, J=16.4, 8.0, 4.0 Hz, 2H), 2.34-2.27 (m, 2H), 1.79-1.74 (m, 2H), 1.46-1.41 (m, 2H), 1.09-1.06 (m, 1H), 1.01-0.99 (m, 1H), 0.86 (ddt, J=29.6, 14.7, 7.5 Hz, 2H), 0.61 (dd, J=15.7, 7.1 Hz, 2H), 0.04 (s, 3H); $^{13}$C NMR (150 MHz, MeOD) δ: 157.2 (C), 154.0 (C), 146.8 (C), 126.2 (CH), 123.2 (CH), 120.1 (CH), 119.8 (CH), 70.1 ($CH_2$), 33.2 ($CH_2$), 28.8 ($CH_2$), 28.6 ($CH_2$), 20.9 ($CH_2$), 18.8 ($CH_2$), 18.7 ($CH_2$), 16.9 ($CH_2$), 2.82 ($CH_3$).

(E)-N-(7-(1-(difluoroboranyl)-3,5-dimethyl-1H-pyrrol-2-yl)-7-(3,5-dimethyl-2H-pyrrol-2-ylidene)heptyl)-4-(1-methyl-2,3,6,7-tetrahydro-1H-silepin-1-yl)butanamide.$AgNO_3$ (E)2,5-dioxopyrrolidin-1-yl 4-(1-methyl-2,3,6,7-tetrahydro-1H-silepin-1-yl)butanoate.$AgNO_3$ (0.110 mmol, 7.20 equiv) was treated with 1.5 mL dichloromethane and 2.0 mL brine. The dichloromethane layer was separated. The aqueous layer was extract with 2×1.5 mL dichloromethane. The organic layer was combined and dried with $Na_2SO_4$, filtered and carefully concentrated down to 1.5 mL via rotary evaporation. (Z)-7-(1-(difluoroboryl)-3,5-dimethyl-1H-pyrrol-2-yl)-7-(3,5-dimethyl-2H-pyrrol-2-ylidene)heptan-1-amine (BODIPY amine, 5.30 mg, 0.0153 mmol, 1.00 equiv) and triethylamine (40.8 mg, 0.403 mmol, 26.0 equiv) were added. The reaction was stirred at room temperature for 1.5 hour. The reaction mixture was quickly loaded on to flash chromatography, (15%-50% ethyl acetate/hexane) afforded the (E)-N-(7-(1-(difluoroboranyl)-3,5-dimethyl-1H-pyrrol-2-yl)-7-(3,5-dimethyl-2H-pyrrol-2-ylidene)heptyl)-4-(1-methyl-2,3,6,7-tetrahydro-1H-silepin-1-yl)butanamide as a solution in ca. 50% ethyl acetate/hexane. The solution was allowed to flow through a plug of 4 g silica gel (impregnated with 10% w/w $AgNO_3$), which was packed in an 11 g Biotage® SNAP cartridge (contained a bed of unmodified silica gel). The SNAP cartridge was eluted with 100 mL 50% ethyl acetate/hexane over 2 hours. Then the silica gel column was washed with 100 mL 60% ethyl acetate/hexane, followed by 100 mL EtOH to give the desired EtOH solution of (E)-N-(7-(1-(difluoroboranyl)-3,5-dimethyl-1H-pyrrol-2-yl)-7-(3,5-dimethyl-2H-pyrrol-2-ylidene)heptyl)-4-(1-methyl-2,3,6,7-tetrahydro-1H-silepin-1-yl)butanamide.$AgNO_3$. The ethanol solution was concentrated via rotary evaporation, affording the (E)-N-(7-(1-(difluoroboranyl)-3,5-dimethyl-1H-pyrrol-2-yl)-7-(3,5-dimethyl-2H-pyrrol-2-ylidene)heptyl)-4-(1-methyl-2,3,6,7-tetrahydro-1H-silepin-1-yl)butanamide.$AgNO_3$ (0.0104 mmol by NMR analysis 68% NMR yield) as orange sticky semisolid.

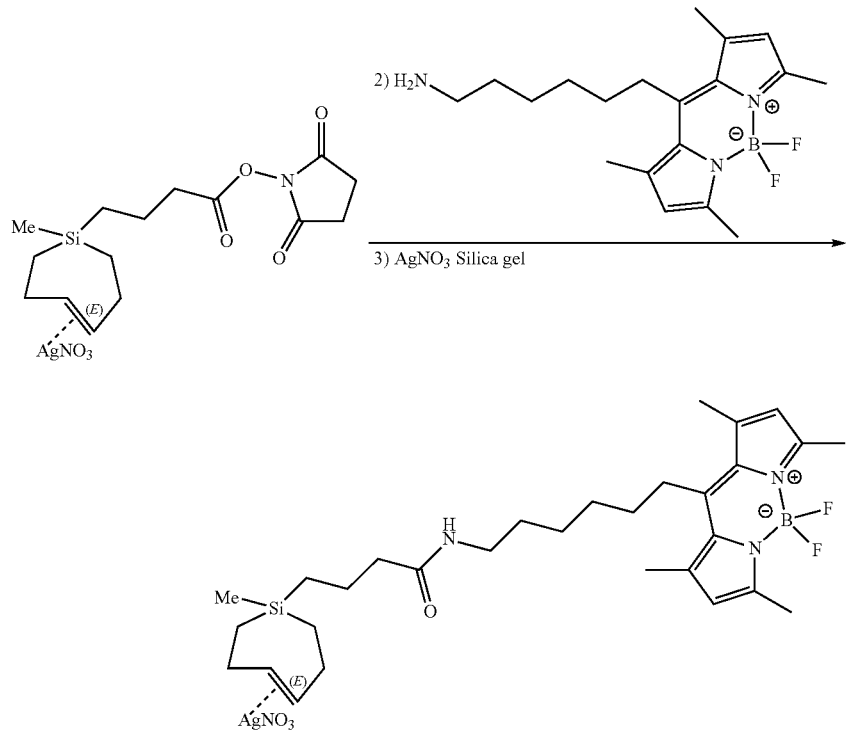

4-(1-methyl-2,3,6,7-tetrahydro-1H-silepin-1-yl)butyl (2-((5-(dimethylamino)naphthalene)-1-sulfonamido)ethyl)carbamate.AgNO₃

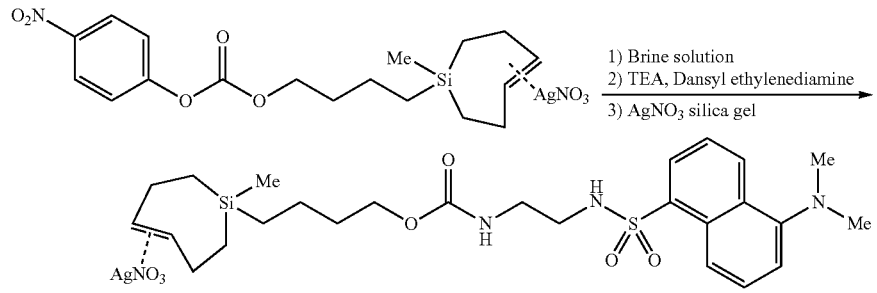

(E) 4-(1-methyl-2,3,6,7-tetrahydro-1H-silepin-1-yl)butyl (4-nitrophenyl) carbonate.AgNO₃ (0.042 mmol) was treated with 2 mL dichloromethane and 3 mL brine. Organic layer was separated. The aqueous layer was extract with 2 mL dichloromethane. The organic layer was combined and dried with Na₂SO₄. The dichloromethane solution of (E) 4-(1-methyl-2,3,6,7-tetrahydro-1H-silepin-1-yl)butyl (4-nitrophenyl) carbonate was transferred to a 10 mL flame-dried flask. Then dansyl ethylenediamine (124 mg, 0.42 mmol, 10 equiv) and triethylamine (TEA, 17.2 mg, 0.17 mmol, 4.0 equiv) was added to the solution. The reaction was stirred at room temperature over 2.5 h. After reaction, the mixture was loaded onto silica gel column directly. Purification by flash column chromatography (10% acetone/hexane, R$_f$=) afforded 4-(1-methyl-2,3,6,7-tetrahydro-1H-silepin-1-yl)butyl (2-((5-(dimethylamino)naphthalene)-1-sulfonamido) ethyl)carbamate as a solution in acetone/hexane. The solution was loaded onto a plug of 4 g silica gel (impregnated with 10% w/w AgNO₃), which was packed in an 11 g Biotage® SNAP cartridge (contained a bed of unmodified silica gel). The SNAP cartridge was eluted with 100 mL 30% acetone/hexane over 2.5 h. Then the silica gel column was washed with 160 mL 30% acetone/hexane, followed by 150 mL EtOH to give the desired EtOH solution of 4-(1-methyl-2,3,6,7-tetrahydro-1H-silepin-1-yl)butyl (2-((5-(dimethylamino)naphthalene)-1-sulfonamido)ethyl)carbamate. The ethanol solution was concentrated via rotary evaporation, affording the 4-(1-methyl-2,3,6,7-tetrahydro-1H-silepin-1-yl)butyl (2-((5-(dimethylamino)naphthalene)-1-sulfona-mido)ethyl)carbamate silver complex (40% NMR yield) as white sticky oil. ¹H NMR (600 MHz, MeOD) δ: 8.57 (d, J=8.5 Hz, 1H), 8.32 (d, J=8.6 Hz, 1H), 8.19 (dd, J=7.3, 1.1 Hz, 1H), 7.59 (dd, J=16.0, 8.5 Hz, 2H), 7.28 (d, J=7.4 Hz, 1H), 5.59-5.51 (m, 2H), 3.95 (t, J=6.3 Hz, 2H), 3.09 (t, J=6.4, 2H), 2.92 (t, J=6.4, 2H), 2.89 (s, 6H), 2.52-2.49 (m, 2H), 2.31-2.26 (m, 2H), 1.59-1.55 (m, 2H), 1.06-1.01 (m, 1H), 0.98-0.89 (m, 2H), 0.88-0.83 (m, 2H), 0.81-0.76 (m, 1H), 0.55 (tt, J=14.3, 7.2 Hz, 2H), −0.01 (s, 3H); ¹³C NMR (150 MHz, MeOD) δ: 153.2 (C), 136.7 (C), 132.3 (C), 131.13 (C), 131.08 (CH), 130.8 (C), 130.1 (CH), 129.8 (CH), 128.9 (CH), 124.2 (CH), 120.2 (CH), 119.9 (CH), 116.2 (CH), 69.0 (CH₂), 65.4 (CH₂), 45.8 (CH₃), 43.5 (CH₂), 33.7 (CH₂), 30.6 (CH₂), 28.7 (CH₂), 28.6 (CH₂), 21.0 (CH₂), 18.7 (CH₂), 16.1 (CH₂), −2.81 (CH₃).

4-(1-methyl-2,3,6,7-tetrahydro-1H-silepin-1-yl)butyl (2-(2-((6-chlorohexyl)oxy)ethoxy)ethyl)carbamate and its Silver Complex

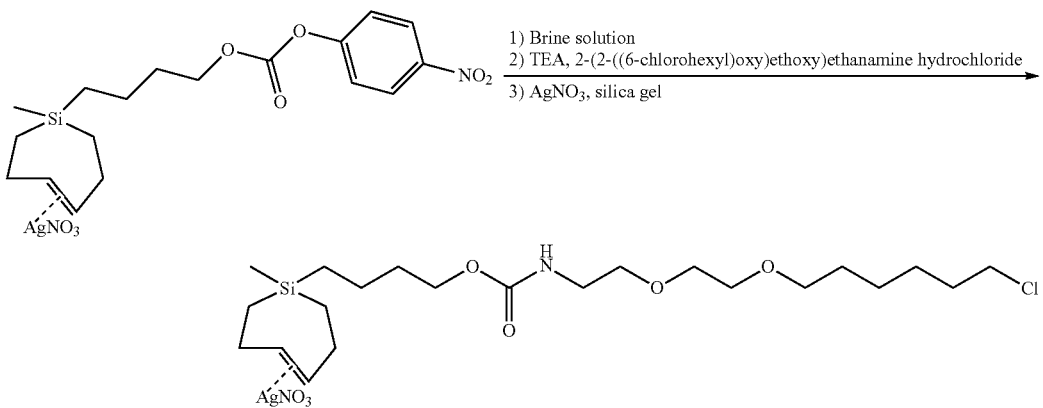

0.255 mmol of (E) 4-(1-methyl-2,3,6,7-tetrahydro-1H-silepin-1-yl)butyl (4-nitrophenyl) carbonate silver complex was treated with 2 mL dichloromethane and 2 mL brine. Organic layer was separated. The aqueous layer was extract with 1.3 mL dichloromethane. The organic layer was combined and dried with Na₂SO₄. The dichloromethane solution of (E) 4-(1-methyl-2,3,6,7-tetrahydro-1H-silepin-1-yl)butyl (4-nitrophenyl) carbonate was transferred to a 10 mL flame-dried flask. Then 2-(2-((6-chlorohexyl)oxy)ethoxy)ethan-amine hydrochloride (33.2 mg, 0.12 mmol, 1.0 equiv) and TEA (88.9 μL, 0.64 mmol, 5.3 equiv) was added to the solution. The reaction was stirred at room temperature over 2.5 h. After reaction, the mixture was loaded onto silica gel column directly. Purification by flash column chromatography (10% acetone/hexane, R_f=) afforded 4-(1-methyl-2,3,6,7-tetrahydro-1H-silepin-1-yl)butyl (2-(2-((6-chlorohexyl)oxy)ethoxy)ethyl)carbamate as a solution in acetone/hexane. The solution was loaded onto a plug of 265 mg silica gel (impregnated with 10% w/w AgNO_3), which was packed in an 11 g Biotage® SNAP cartridge (contained a bed of unmodified silica gel). The SNAP cartridge was eluted with 100 mL 30% acetone/hexane over 2.5 h. Then the silica gel column was washed with 100 mL 30% acetone/hexane, followed by 150 mL EtOH to give the desired EtOH solution of 4-(1-methyl-2,3,6,7-tetrahydro-1H-silepin-1-yl)butyl (2-(2-((6-chlorohexyl)oxy)ethoxy)ethyl)carbamate. The ethanol solution was concentrated via rotary evaporation, affording the 4-(1-methyl-2,3,6,7-tetrahydro-1H-silepin-1-yl)butyl (2-(2-((6-chlorohexyl)oxy)ethoxy)ethyl)carbamate silver complex (40% NMR yield) as white sticky oil. $^1$H NMR (600 MHz, MeOD) δ: 5.61-5.53 (m, 2H), 4.04 (t, J=6.3 Hz, 2H), 3.61-3.55 (m, 6H), 3.53 (t, J=5.6 Hz, 2H), 3.49 (t, J=6.6 Hz, 2H), 3.28 (t, J=5.5 Hz, 2H), 2.55-2.52 (m, 2H), 2.33-2.27 (m, 2H), 1.80-1.75 (m, 2H), 1.66-1.58 (m, 4H), 1.47 (dt, J=14.4, 7.1 Hz, 2H), 1.42-1.36 (m, 4H), 1.09-1.05 (m, 1H), 1.03-0.98 (m, 1H), 0.88 (dt, J=14.8, 7.5 Hz, 1H), 0.82 (dt, J=14.8, 7.6 Hz, 1H), 0.63-0.54 (m, 2H), 0.02 (s, 3H); $^{13}$C NMR (150 MHz, MeOD) δ: 120.1 (CH), 119.9 (CH), 72.2 (CH_2), 71.2 (CH_2), 71.1 (CH_2), 71.0 (CH_2), 65.4 (CH_2), 45.7 (CH_2), 33.9 (CH_2), 33.7 (CH_2), 30.5 (CH_2), 28.73 (CH_2), 28.69 (CH_2), 27.7 (CH_2), 26.4 (CH_2), 21.1 (CH_2), 18.81 (CH_2), 18.78 (CH_2), 16.2 (CH_2), −2.8 (CH_3).

(E)-1,1-dimethyl-2,3,6,7-tetrahydro-1H-silepin-3-yl benzylcarbamate

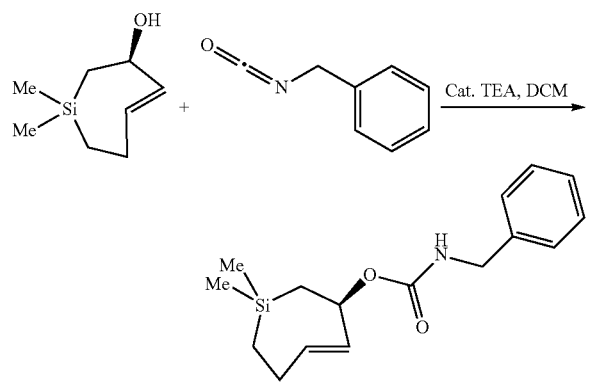

To a solution of (E)-1,1-dimethyl-2,3,6,7-tetrahydro-1H-silepin-3-ol (equatorial isomer 28 mg, 0.18 mmol) in dichloromethane (2 mL) were added benzyl isocyanate (68 μL, 73 mg, 0.55 mmol, 3.0 equiv.) and two drops of triethylamine. The solution was stirred under a nitrogen atmosphere at room temperature for 12 hours. The volatiles were removed and the residue was purified by column chromatography to give the title compound (15 mg, 30% yield) as a colorless oil.

What is claimed is:

1. A substituted trans-cycloheptene according to formula (I)

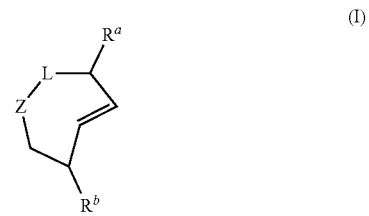

wherein:
a) Z and L are each selected from the group consisting of SiR$^1$R$^2$, CH_2, CHOH, and CHR$^2$; R$^1$ is phenyl or CH_3; R$^2$ is phenyl, CH_3, (CH_2)_nCN, or (CH_2)_nOH, wherein n is an integer from 1 to 5; R$^a$ and R$^b$ are each individually selected from the group consisting of H, OH, and CH_3; and Z and L are not both SiR$^1$R$^2$; or
b) Z is BocN, L is CH_2, R$^a$ is H, and R$^b$ is H; or
c) Z is C=O, L is CH_2, R$^a$ is H, and R$^b$ is H.

2. The substituted trans-cycloheptene according to claim 1, wherein Z, L, R$^a$, and R$^b$ are according to any one of combinations a) through l):
a) Z is CHOH, L is CH_2, R$^a$ is H, and R$^b$ is H;
b) Z is CH_2CHOH, L is CH_2, R$^a$ is H, and R$^b$ is H;
c) Z is CH_2, L is CH_2, and R$^a$ is OH, and R$^b$ is H;
d) Z is CH_2, L is CHOH, R$^a$ is OH, and R$^b$ is H;
e) Z is BocN, L is CH_2, R$^a$ is H, and R$^b$ is H;
f) Z is C=O, L is CH_2, R$^a$ is H, and R$^b$ is H;
g) Z is SiR$^1$R$^2$, L is CH_2, R$^a$ is H, R$^b$ is H, R$^1$ is CH_3, and R$^2$ is either (CH_2)_3CN or (CH_2)_4OH;
h) Z is SiCH_3(CH_2)_3OH, L is CH_2, R$^a$ is CH_3, and R$^b$ is CH_3;
i) Z is SiPh_2, L is CH_2, R$^a$ is H, and R$^b$ is H;
j) Z is Si(CH_3)_2, L is CH_2, R$^a$ is OH, and R$^b$ is H;
k) Z is CH_2, L is SiPh_2, R$^a$ is H, and R$^b$ is H;
l) Z is CH_2, L is SiCH_3(CH_2)_4OH, R$^a$ is H, R$^b$ is H.

3. A method of performing a bioorthogonal coupling reaction, comprising contacting a tetrazine, ketene, conjugated diene, or 1,3-dipole, in each case substituted with a biomolecule, with a trans-cycloheptene or a hetero-trans-cycloheptene according to claim 1.

* * * * *